US008492348B2

(12) United States Patent
Mochly-Rosen et al.

(10) Patent No.: US 8,492,348 B2
(45) Date of Patent: *Jul. 23, 2013

(54) METHODS OF INCREASING CEREBRAL BLOOD FLOW

(75) Inventors: Daria Mochly-Rosen, Menlo Park, CA (US); Rachel Bright, Claremont, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 640 days.

This patent is subject to a terminal disclaimer.

(21) Appl. No.: 12/490,097

(22) Filed: Jun. 23, 2009

(65) Prior Publication Data
US 2009/0270328 A1    Oct. 29, 2009

Related U.S. Application Data

(63) Continuation of application No. 11/317,806, filed on Dec. 23, 2005, now Pat. No. 7,563,772.

(60) Provisional application No. 60/641,413, filed on Jan. 4, 2005.

(51) Int. Cl.
A61K 38/08    (2006.01)
A61K 38/16    (2006.01)

(52) U.S. Cl.
USPC ........... 514/21.7; 514/21.3; 514/7.5; 530/328

(58) Field of Classification Search
None
See application file for complete search history.

(56) References Cited

U.S. PATENT DOCUMENTS

| | | | |
|---|---|---|---|
| 4,708,871 A | 11/1987 | Geysen | |
| 5,057,614 A | 10/1991 | Davis et al. | |
| 5,380,746 A | 1/1995 | Barth et al. | |
| 5,559,228 A | 9/1996 | Gillig et al. | |
| 5,776,716 A | 7/1998 | Ron et al. | |
| 5,783,405 A | 7/1998 | Mochly-Rosen et al. | |
| 5,804,604 A | 9/1998 | Frankel et al. | |
| 6,165,977 A | 12/2000 | Mochly-Rosen | |
| 6,255,057 B1 | 7/2001 | Gordon et al. | |
| 6,391,888 B1 | 5/2002 | Gleich | |
| 6,855,693 B2 | 2/2005 | Mochly-Rosen et al. | |
| 6,993,275 B2 * | 1/2006 | Mitsuya et al. | 399/301 |
| 7,563,772 B2 * | 7/2009 | Mochly-Rosen et al. | 514/1.1 |
| 7,803,775 B2 * | 9/2010 | Mochly-Rosen et al. | 514/7.5 |
| 2002/0048582 A1 | 4/2002 | King | |
| 2002/0150984 A1 * | 10/2002 | Mochly-Rosen et al. | 435/69.1 |
| 2003/0134774 A1 | 7/2003 | Steinberg et al. | |
| 2003/0143656 A1 * | 7/2003 | Alessi et al. | 435/15 |
| 2003/0211109 A1 | 11/2003 | King | |
| 2004/0204364 A1 | 10/2004 | Mochly-Rosen et al. | |
| 2004/0259816 A1 | 12/2004 | Pandol et al. | |
| 2005/0164324 A1 * | 7/2005 | Gygi | 435/23 |
| 2005/0267030 A1 | 12/2005 | Tsao et al. | |

FOREIGN PATENT DOCUMENTS

| | | |
|---|---|---|
| WO | WO 97/14038 | 4/1997 |
| WO | WO 01/28543 A1 | 4/2001 |
| WO | WO 02/057413 A2 | 7/2002 |
| WO | WO 02/057413 A3 | 7/2002 |

OTHER PUBLICATIONS

Aley, K. O., R. O. Messing, et al. (2000). "Chronic hypersensitivity for inflammatory nociceptor sensitization mediated by the epsilon isozyme of protein kinase C." J Neurosci 20(12): 4680-5.
Altschul et al., *Nucleic Acids Res.*, 25:3389-3402 (1997).
Altschul, et al., *J. Mol. Biol.*, 215:403-410 (1990).
Armstrong et al., "Preconditioning of Isolated Rabbit Cardiomycyes: Induction by Metabolic Stress and Blockade by the Adenosine Antagonist SPT and Calphostin C, a Protein Kinase C Inhibitor", *Cardiovascular Research*, 28:72-77 (1994).
Baird, A. E. and Warach, S., *J., Cereb. Blood Flow Metab.*, 18:583-609 (1998).
Banci, L., G. Cavallaro, et al. (2002). "Molecular dynamics characterization of the C2 domain of protein kinase Cbeta." J Biol Chem 277(15): 12988-97.
Baudier, J., D. Mochly-Rosen, et al. (1987). "Comparison of S100b protein with calmodulin: interactions with melittin and microtubule-associated tau proteins and inhibition of phosphorylation of tau proteins by protein kinase C." Biochemistry 26(10): 2886-93.
Begley, R., T. Liron, et al. (2004). "Biodistribution of intracellularly acting peptides conjugated reversibly to Tat." Biochem Biophys Res Commun 318(4): 949-54.
Bollag, G. E., R. A. Roth, et al. (1986). "Protein kinase C directly phosphorylates the insulin receptor in vitro and reduces its protein-tyrosine kinase activity." Proc Natl Acad Sci U S A 83(16): 5822-4.
Borlongan et al., *Brain Res.*, 1010(1-2):108-116 (2004).
Braun, M. U. and D. Mochly-Rosen (2003). "Opposing effects of delta- and zeta-protein kinase C isozymes on cardiac fibroblast proliferation: use of isozyme-selective inhibitors." J Mol Cell Cardiol 35(8): 895-903.

(Continued)

*Primary Examiner* — Satyanarayana R Gudibande
(74) *Attorney, Agent, or Firm* — McDermott Will & Emery LLP

(57) ABSTRACT

Methods of increasing blood flow in a mammalian brain blood vessel characterized by, or otherwise experiencing, decreased blood flow due to an ischemic or other hypoxic event, vasoconstriction or vasospasm following hemorrhagic stroke; due to chronic high blood pressure; and/or due to idiopathic causes are provided. The method for increasing blood flow in such a mammalian brain blood vessel includes administering to a patient in need thereof a therapeutically effective amount of an inhibitor of δ protein kinase C. In certain embodiments, the inhibitor can be chronically administered without causing desensitization of the patient to the inhibitor. Kits for increasing blood flow in a mammalian brain blood vessel characterized by, or otherwise experiencing, decreased blood flow due to an ischemic or other hypoxic event, vasoconstriction or vasospasm following hemorrhagic stroke; due to chronic high blood pressure; and/or due to idiopathic causes are provided.

19 Claims, 4 Drawing Sheets

OTHER PUBLICATIONS

Bright, R. and D. Mochly-Rosen (2005). "The role of protein kinase C in cerebral ischemic and reperfusion injury." Stroke 36(12): 2781-90.
Bright, R., A. P. Raval, et al. (2004). "Protein kinase C delta mediates cerebral reperfusion injury in vivo." J Neurosci 24(31): 6880-8.
Bright et al., *Neurology*, 60(5 Supplement 1):A64 (2003).
Bright et al., *Society for Neuroscience Abstract Viewer and Itinerary Planner*, 2002: Abstract No. 301.14 (2002).
Brzoska, P. M., H. Chen, et al. (1995). "The product of the ataxia-telangiectasia group D complementing gene, ATDC, interacts with a protein kinase C substrate and inhibitor." Proc Natl Acad Sci U S A 92(17): 7824-8.
Calamante et al., *J. Cereb. Blood Flow Metab.*, 19:701-735 (1999).
Cardone, M. H., B. L. Smith, et al. (1994). "Phorbol myristate acetate-mediated stimulation of transcytosis and apical recycling in MDCK cells." J Cell Biol 124(5): 717-27.
Cardone, M. H., B. L. Smith, et al. (1996). "Signal transduction by the polymeric immunoglobulin receptor suggests a role in regulation of receptor transcytosis." J Cell Biol 133(5): 997-1005.
Chang, Q. and Tepperman, B.L., "Effect of Selective PKC Isoform Activation and Inhibition on TNF-α-Induced Injury and Apoptosis in Human Intestinal Epithelial Cells", *British Journal of Pharmacology*, 140:41-52 (2003).
Chen, C. and D. Mochly-Rosen (2001). "Opposing effects of delta and xi PKC in ethanol-induced cardioprotection." J Mol Cell Cardiol 33(3): 581-5.
Chen, C. H., M. O. Gray, et al. (1999). "Cardioprotection from ischemia by a brief exposure to physiological levels of ethanol: role of epsilon protein kinase C." Proc Natl Acad Sci U S A 96(22): 12784-9.
Chen, L., H. Hahn, et al. (2001). "Opposing cardioprotective actions and parallel hypertrophic effects of delta PKC and epsilon PKC." Proc Natl Acad Sci U S A 98(20): 11114-9.
Chen, L., L. R. Wright, et al. (2001). "Molecular transporters for peptides: delivery of a cardioprotective epsilonPKC agonist peptide into cells and intact ischemic heart using a transport system, R(7)." Chem Biol 8(12): 1123-9.
Chou Wen-Hai et al., *Journal of Clinical Investiagtion*, 114(1):49-56 (2004).
Csukai, M. and D. Mochly-Rosen (1998). "Molecular genetic approaches. II. Expression-interaction cloning." Methods Mol Biol 88:133-9.
Csukai, M. and D. Mochly-Rosen (1999). "Pharmacologic modulation of protein kinase C isozymes: the role of RACKs and subcellular localisation." Pharmacol Res 39(4):253-9.
Csukai, M., C. H. Chen, et al. (1997). "The coatomer protein beta'-COP, a selective binding protein (RACK) for protein kinase Cepsilon." J Biol Chem 272(46):29200-6.
Dell, E. J., J. Connor, et al. (2002). "The betagamma subunit of heterotrimeric G proteins interacts with RACK1 and two other WD repeat proteins." J Biol Chem 277(51): 49888-95.
Dempsey, E. C., A. C. Newton, et al. (2000). "Protein kinase C isozymes and the regulation of diverse cell responses." Am J Physiol Lung Cell Mol Physiol 279(3): L429-38.
Diamond, I., L. Nagy, et al. (1991). "The role of adenosine and adenosine transport in ethanol-induced cellular tolerance and dependence. Possible biologic and genetic markers of alcoholism." Ann N Y Acad Sci 625:473-87.
Disatnik, M. H., A. R. Winnier, et al. (1994). "Distinct responses of protein kinase C isozymes to c-erbB-2 activation in SKBR-3 human breast carcinoma cells." Cell Growth Differ 5(8):873-80.
Disatnik, M. H., G. Buraggi, et al. (1994). "Localization of protein kinase C isozymes in cardiac myocytes." Exp Cell Res 210(2):287-97.
Disatnik, M. H., S. M. Hernandez-Sotomayor, et al. (1994). "Phospholipase C-gamma 1 binding to intracellular receptors for activated protein kinase C." Proc Natl Acad Sci U S A 91(2): 559-63.
Disatnik, M. H., S. N. Jones, et al. (1995). "Stimulus-dependent subcellular localization of activated protein kinase C; a study with acidic fibroblast growth factor and transforming growth factor-beta 1 in cardiac myocytes." J Mol Cell Cardiol 27(11): 2473-81.

Disatnik et al., "Sequential Activation of Individual PKC Isozymes in Integrin-Mediated Muscle Cell Spreading: A Role fo MARCKS in an Integrin Signaling Pathway", *Journal fo Cell Science*, 115:2151-2163 (2002).
Dorn, G. W., 2nd and D. Mochly-Rosen (2002). "Intracellular transport mechanisms of signal transducers." Annu Rev Physiol 64: 407-29.
Dorn, G. W., 2nd, M. C. Souroujon, et al. (1999). "Sustained in vivo cardiac protection by a rationally designed peptide that causes epsilon protein kinase C translocation." Proc Natl Acad Sci U S A 96(22): 12798-803.
Endemann, G. and D. Mochly-Rosen (2003). "Methods for detecting binding proteins: an introduction." Methods Mol Biol 233:307-25.
Endemann, G., D. Schechtman, et al. (2003). "Cytotoxicity of pEGFP vector is due to residues encoded by multiple cloning site." Anal Biochem 313(2):345-7.
Freidinger, R.M. "Design and Synthesis of Novel Bioactive Peptides and Peptidomimetics" *J. Med. Chem.*, 46:5553-5566 (2003).
Fuchs, S., D. Bartfeld, et al. (1980). "Immune regulation of experimental myasthenia." J Neurol Neurosurg Psychiatry 43(7): 634-43.
Fuchs, S., D. Bartfeld, et al. (1981). "Acetylcholine receptor: molecular dissection and monoclonal antibodies in the study of experimental myasthenia." Ann N Y Acad Sci 377: 110-24.
Fuchs, S., D. Bartfeld, et al. (1981). "Molecular aspects of experimental autoimmune myasthenia gravis." Prog Clin Biol Res 63: 405-17.
Fukuda, O., *Neurosurgery*, 36(2):358-364 (1995).
Garcia-Navarro, S., Y. Marantz, et al. (1994). "Developmental expression of protein kinase C subspecies in rat brain-pituitary axis." Mol Cell Endocrinol 103(1-2): 133-8.
Genbank Accession No. AAT48070, retrieved on Dec. 28, 2006.
Genbank Accession No. AAH76505, *Rattus norvegieus*, retrieved on Dec. 28, 2006.
Genbank Accession No. BAA01381, *Human δPKC*, retrieved on Dec. 28, 2006.
Ginsberg et al., *J. Cereb Blood Flow Metab.*, 2(1):89-98 (1982).
Goldberg, G., D. Mochly-Rosen, et al. (1983). "Monoclonal antibodies modify acetylcholine-induced ionic channel properties in cultured chick myoballs." J Membr Biol 76(2): 123-8.
Gordon, A. S., L. Nagy, et al. (1990). "Chronic ethanol-induced heterologous desensitization is mediated by changes in adenosine transport." Biochem Soc Symp 56: 117-36.
Gray, M. O., H. Z. Zhou, et al. (2004). "Preservation of base-line hemodynamic function and loss of inducible cardioprotection in adult mice lacking protein kinase C epsilon." J Biol Chem 279(5): 3596-604.
Gray, M. O., J. S. Karliner, et al. (1997). "A selective epsilon-protein kinase C antagonist inhibits protection of cardiac myocytes from hypoxia-induced cell death." J Biol Chem 272(49): 30945-51.
Hool, Livia C., "Protein Kinase C Isozyme Selective Peptides—A Current View of What They Tell Us About Location and Function of Isozymes in the Heart", *Current Pharmaceutical Design*, 11:549-559 (2005).
Hu, K., D. Mochly-Rosen, et al. (2000). "Evidence for functional role of epsilonPKC isozyme in the regulation of cardiac Ca(2+) channels." Am J Physiol Heart Circ Physiol 279(6): H2658-64.
Hundle, B., T. McMahon, et al. (1997). "An inhibitory fragment derived from protein kinase Cepsilon prevents enhancement of nerve growth factor responses by ethanol and phorbol esters." J Biol Chem 272(23): 15028-35.
Inagaki, K., Y. Kihara, et al. (2000). "Anti-ischemic effect of a novel cardioprotective agent, JTV519, is mediated through specific activation of delta-isoform of protein kinase C in rat ventricular myocardium." Circulation 101(7): 797-804.
Inagaki, K., Y. Iwanaga, et al. (2002). "Tissue angiotensin II during progression or ventricular hypertrophy to heart failure in hypertensive rats; differential effects on PKC epsilon and PKC beta." J Mol Cell Cardiol 34(10): 1377-85.
Inagaki, K., H. S. Hahn, et al. (2003). "Additive protection of the ischemic heart ex vivo by combined treatment with delta-protein kinase C inhibitor and epsilon-protein kinase C activator." Circulation 108(7): 869-75.

Inagaki, K., L. Chen, et al. (2003). "Inhibition of delta-protein kinase C protects against reperfusion injury of the ischemic heart in vivo." Circulation 108(19): 2304-7.

Inagaki, K., R. Begley, et al. (2005). "Cardioprotection by epsilon-protein kinase C activation from ischemia: continuous delivery and antiarrhythmic effect of an epsilon-protein kinase C-activating peptide." Circulation 111(1): 44-50.

Jin, Z. Q., H. Z. Zhou, et al. (2002). "Cardioprotection mediated by sphingosine-1-phosphate and ganglioside GM-1 in wild-type and PKC epsilon knockout mouse hearts." Am J Physiol Heart Circ Physiol 282(6): H1970-7.

Johnson, J. A. and D. Mochly-Rosen (1995). "Inhibition of the spontaneous rate of contraction of neonatal cardiac myocytes by protein kinase C isozymes. A putative role for the epsilon isozyme." Circ Res 76(4): 654-63.

Johnson, J. A., M. O. Gray, et al. (1996). "A protein kinase C translocation inhibitor as an isozyme-selective antagonist of cardiac function." J Biol Chem 271(40): 24962-6.

Johnson, J. A., M. O. Gray, et al. (1996). "An improved permeabilization protocol for the introduction of peptides into cardiac myocytes. Application to protein kinase C research." Circ Res 79(6): 1086-99.

Johnson, J. A., S. Adak, et al. (1995). "Prolonged phorbol ester treatmentdown-regulates protein kinase C isozymes and increases contraction rate in neonatal cardiac myocytes." Life Sci 57(11): 1027-38.

Karlin and Altschul, *PNAS*, 90:5873-5877 (1993).

Karlin and Altschul. *PNAS*, 87:2264-2268 (1990).

Knauf, J. A., L. S. Ward, et al. (2002). "Isozyme-specific abnormalities of PKC in thyroid cancer: evidence for post-transcriptional changes in PKC epsilon." J Clin Endocrinol Metab 87(5): 2150-9.

Knauf, J. A., R. Elisei, et al. (1999). "Involvement of protein kinase Cepsilon (PKCepsilon) in thyroid cell death. A truncated chimeric PKCepsilon cloned from a thyroid cancer cell line protects thyroid cells from apoptosis." J Biol Chem 274(33): 23414-25.

Koponen, S., K. Kurkinen, et al. (2003). "Prevention of NMDA-induced death of cortical neurons by inhibition of protein kinase Czeta." J Neurochem 86(2): 442-50.

Krauss, S. W., D. Mochly-Rosen, et al. (1987). "Exposure of HeLa DNA polymerase alpha to protein kinase C affects its catalytic properties." J Biol Chem 262(8): 3432-5.

Lange-Asschenfeldt, C., A. P. Raval, et al. (2004). "Epsilon protein kinase C mediated ischemic tolerance requires activation of the extracellular regulated kinase pathway in the organotypic hippocampal slice." J Cereb Blood Flow Metab 24(6): 636-45.

Laudanna, C., D. Mochly-Rosen, et al. (1998). "Evidence of zeta protein kinase C involvement in polymorphonuclear neutrophil integrin-dependent adhesion and chemotaxis." J Biol Chem 273(46): 30306-15.

Leenders et al. *Brain*, 113:27-47 (1990).

Liu, G. S., M. V. Cohen, et al. (1999). "Protein kinase C-epsilon is responsible for the protection of preconditioning in rabbit cardiomyocytes." J Mol Cell Cardiol 31(10): 1937-48.

Mackay, K. and D. Mochly-Rosen (1999). "An inhibitor of p38 mitogen-activated protein kinase protects neonatal cardiac myocytes from ischemia." J Biol Chem 274(10): 6272-9.

Mackay, K. and D. Mochly-Rosen (2000). "Involvement of a p38 mitogen-activated protein kinase phosphatase in protecting neonatal rat cardiac myocytes from ischemia." J Mol Cell Cardiol 32(8): 1585-8.

Mackay, K. and D. Mochly-Rosen (2001). "Arachidonic acid protects neonatal rat cardiac myocytes from ischaemic injury through epsilon protein kinase C." Cardiovasc Res 50(1): 65-74.

Mackay, K. and D. Mochly-Rosen (2001). "Localization, anchoring, and functions of protein kinase C isozymes in the heart." J Mol Cell Cardiol 33(7): 1301-7.

Maier et al., *J. Neurosurg.*, 94(1):90-96 (2001).

Miettinen et al., *Journal of Neuroscience*, 16(19):6236-6245 (1996).

Miller, L. D., K. C. Lee, et al. (2004). "RACK1 regulates Src-mediated Sam68 and p190RhoGAP signaling." Oncogene 23(33): 5682-6.

Mihailidou, A. S., M. Mardini, et al. (2004). "Rapid, nongenomic effects of aldosterone in the heart mediated by epsilon protein kinase C." Endocrinology 145(2): 773-80.

Mitchell et al., *J. Peptide Res.*, 56:318-325 (2000).

Miyamae, M., M. M. Rodriguez, et al. (1998). "Activation of epsilon protein kinase C correlates with a cardioprotective effect of regular ethanol consumption." Proc Natl Acad Sci U S A 95(14): 8262-7.

Miyawaki et al., *Circulation Res.*, 80(6):790 (1997).

Mochly-Rosen, D. (1995). "Localization of protein kinases by anchoring proteins: a theme in signal transduction." Science 268(5208): 247-51.

Mochly-Rosen, D. and A. S. Gordon (1990). "GTP-binding proteins are restricted to signal transduction sites." Biochem Biophys Res Commun 173(1): 388-95.

Mochly-Rosen, D. and A. S. Gordon (1998). "Anchoring proteins for protein kinase C: a means for isozyme selectivity." Faseb J 12(1): 35-42.

Mochly-Rosen, D. and D. E. Koshland, Jr. (1987). "Domain structure and phosphorylation of protein kinase C." J Biol Chem 262(5): 2291-7.

Mochly-Rosen, D. and D. E. Koshland, Jr. (1988). "A general procedure for screening inhibitory antibodies: application for identifying anti-protein kinase C antibodies." Anal Biochem 170(1): 31-7.

Mochly-Rosen, D. and L. M. Kauvar (1998). "Modulating protein kinase C signal transduction." Adv Pharmacol 44: 91-145.

Mochly-Rosen, D. and L. M. Kauvar (2000). "Pharmacological regulation of network kinetics by protein kinase C localization." Semin Immunol 12(1): 55-61.

Mochly-Rosen, D. and S. Fuchs (1981). "Monoclonal anti-acetylcholine-receptor antibodies directed against the cholinergic binding site." Biochemistry 20(20): 5920-4.

Mochly-Rosen, D., A. I. Basbaum, et al. (1987). "Distinct cellular and regional localization of immunoreactive protein kinase C in rat brain." Proc Natl Acad Sci U S A 84(13): 4660-4.

Mochly-Rosen, D., B. L. Smith, et al. (1995). "Interaction of protein kinase C with RACK1, a receptor for activated C-kinase: a role in beta protein kinase C mediated signal transduction." Biochem Soc Trans 23(3): 596-600.

Mochly-Rosen, D., C. J. Henrich, et al. (1990). "A protein kinase C isozyme is translocated to cytoskeletal elements on activation." Cell Regul 1(9): 693-706.

Mochly-Rosen, D., F. H. Chang, et al. (1988). "Chronic ethanol causes heterologous desensitization of receptors by reducing alpha s messenger RNA." Nature 333(6176): 848-50.

Mochly-Rosen, D., G. Wu, et al. (2000). "Cardiotrophic effects of protein kinase C epsilon: analysis by in vivo modulation of PKCepsilon translocation." Circ Res 86(11): 1173-9.

Mochly-Rosen, D., H. Khaner, et al. (1991). "Identification of intracellular receptor proteins for activated protein kinase C." Proc Natl Acad Sci U S A 88(9): 3997-4000.

Mochly-Rosen, D., H. Khaner, et al. (1991). "Intracellular receptors for activated protein kinase C. Identification of a binding site for the enzyme." J Biol Chem 266(23): 14866-8.

Mochly-Rosen, D., J. A. Fagin, et al. (2001). "Spontaneous occurrence of an inhibitor of protein kinase C localization in a thyroid cancer cell line: role in thyroid tumorigenesis." Adv Enzyme Regul 41: 87-97.

Mochly-Rosen, *Science*, 268:247-251 (1995).

Mochly-Rosen, D., K. G. Miller, et al. (1992). "p65 fragments, homologous to the C2 region of protein kinase C, bind to the intracellular receptors for protein kinase C." Biochemistry 31(35): 8120-4.

Murriel, C. L. and D. Mochly-Rosen (2003). "Opposing roles of delta and epsilonPKC in cardiac ischemia and reperfusion: targeting the apoptotic machinery." Arch Biochem Biophys 420(2): 246-54.

Murriel, C. L., E. Churchill, et al. (2004). "Protein kinase Cdelta activation induces apoptosis in response to cardiac ischemia and reperfusion damage: a mechanism involving BAD and the mitochondria." J Biol Chem 279(46): 47985-91.

Nishizawa Shigeru et al., *Journal of Vascular Research*, 40(2):169-178 (2003).

Nelson, E. J., K. Hellevuo, et al. (2003). "Ethanol-induced phosphorylation and potentiation of the activity of type 7 adenylyl cyclase. Involvement of protein kinase C delta." J Biol Chem 278(7): 4552-60.

Novalija, E., L. G. Kevin, et al. (2003). "Reactive oxygen species precede the epsilon isoform of protein kinase C in the anesthetic preconditioning signaling cascade." Anesthesiology 99(2): 421-8.

Ono et al., *Journal of Biological Chemistry*, 263(14):6927-6932 (1988).

Pastori, R. L., D. Klein, et al. (2004). "Delivery of proteins and peptides into live cells by means of protein transduction domains: potential application to organ and cell transplantation." Transplantation 77(11): 1627-31.

Perez, O. D., D. Mitchell, et al. (2003). "Leukocyte functional antigen 1 lowers T cell activation thresholds and signaling through cytohesin-1 and Jun-activating binding protein 1." Nat Immunol 4(11): 1083-92.

Perez-Pinzon et al., *J. Neurolog. Sci.*, 153(1):25-31 (1997).

Pitchford, S., J. W. Day, et al. (1992). "Nicotinic acetylcholine receptor desensitization is regulated by activation-induced extracellular adenosine accumulation." J Neurosci 12(11): 4540-4.

Pizzighella, S., A. S. Gordon, et al. (1983). "An anti-acetylcholine receptor monoclonal antibody cross-reacts with phosvitin." FEBS Lett 159(1-2): 246-50.

Raval, A. P., K. R. Dave, et al. (2003). "Epsilon PKC is required for the induction of tolerance by ischemic and NMDA-mediated preconditioning in the organotypic hippocampal slice." J Neurosci 23(2): 384-91.

Rempp et al, *Radiology*, 193:637-641 (1994).

Ridge, K. M., L. Dada, et al. (2002). "Dopamine-induced exocytosis of Na,K-ATPase is dependent on activation of protein kinase C-epsilon and -delta." Mol Biol Cell 13(4): 1381-9.

Rodriguez, M. M., C. H. Chen, et al. (1999). "Characterization of the binding and phosphorylation of cardiac calsequestrin by epsilon protein kinase C." FEBS Lett 454(3): 240-6.

Rodriguez, M. M., D. Ron, et al. (1999). "RACK1, a protein kinase C anchoring protein, coordinates the binding of activated protein kinase C and select pleckstrin homology domains in vitro." Biochemistry 38(42): 13787-94.

Rodriguez et al., *Stroke*, 18(1):13-20 (1987).

Ron, D. and D. Mochly-Rosen (1994). "Agonists and antagonists of protein kinase C function, derived from its binding proteins." J Biol Chem 269(34): 21395-8.

Ron, D. and D. Mochly-Rosen (1995). "An autoregulatory region in protein kinase C: the pseudoanchoring site." Proc Natl Acad Sci U S A 92(2): 492-6.

Ron, D., C. H. Chen, et al. (1994). "Cloning of an intracellular receptor for protein kinase C: a homolog of the beta subunit of G proteins." Proc Natl Acad Sci U S A 91(3): 839-43.

Ron, D., J. Luo, et al. (1995). "C2 region-derived peptides inhibit translocation and function of beta protein kinase C in vivo." J Biol Chem 270(41): 24180-7.

Rothbard et al., *Nature Med.*, 6:1253-1257 (2000).

Satoh, A., A. S. Gukovskaya, et al. (2004). "PKC-delta and -epsilon regulate NF-kappaB activation induced by cholecystokinin and TNF-alpha in pancreatic acinar cells." Am J Physiol Gastrointest Liver Physiol 287(3): G582-91.

Schechtman, D. and D. Mochly-Rosen (2001). "Adaptor proteins in protein kinase C-mediated signal transduction." Oncogene 20(44): 6339-47.

Schechtman, D., C. Murriel, et al. (2003). "Overlay method for detecting protein-protein interactions." Methods Mol Biol 233: 351-7.

Schechtman, D., D. Mochly-Rosen, et al. (2003). "Glutathione S-transferase pull-down assay." Methods Mol Biol 233: 345-50.

Schechtman, D., M. L. Craske, et al. (2004). "A critical intramolecular interaction for protein kinase Cepsilon translocation." J Biol Chem 279(16): 15831-40.

Shizukuda, Y. and P. M. Buttrick (2001). "Protein kinase C(epsilon) modulates apoptosis induced by beta-adrenergic stimulation in adult rat ventricular myocytes via extracellular signal-regulated kinase (ERK) activity." J Mol Cell Cardiol 33(10): 1791-803.

Shizukuda, Y., M. E. Reyland, et al. (2002). "Protein kinase C-delta modulates apoptosis induced by hyperglycemia in adult ventricular myocytes." Am J Physiol Heart Circ Physiol 282(5): H1625-34.

Shizukuda, Y. et al., *Circulation*, 100(18):1909-1916, (1999).

Simon, A. J., S. P. Saville, et al. (1993). "Characterization of PKC2, a gene encoding a second protein kinase C isotype of *Saccharomyces cerevisiae*." Curr Biol 3(12): 813-21.

Simon, A. J., Y. Milner, et al. (1991). "The identification and purification of a mammalian-like protein kinase C in the yeast *Saccharomyces cerevisiae*." Proc Biol Sci 243(1307): 165-71.

Smith, B. L. and D. Mochly-Rosen (1992). "Inhibition of protein kinase C function by injection of intracellular receptors for the enzyme." Biochem Biophys Res Commun 188(3): 1235-40.

Smith, B. L., B. W. Krushelnycky, et al. (1996). "The HIV nef protein associates with protein kinase C theta." J Biol Chem 271(28): 16753-7.

Souroujon, M. C. and D. Mochly-Rosen (1998). "Peptide modulators of protein-protein interactions in intracellular signaling." Nat Biotechnol 16(10): 919-24.

Souroujon, M. C., D. Mochly-Rosen, et al. (1983). "Interaction of monoclonal antibodies to Torpedo acetylcholine receptor with the receptor of skeletal muscle." Muscle Nerve 6(4): 303-11.

Souroujon, M. C., L. Yao, et al. (2004). "State-specific monoclonal antibodies identify an intermediate state in epsilon protein kinase C activation." J Biol Chem 279(17): 17617-24.

Souroujon, M. C., S. Pizzighella, et al. (1985). "Antigenic specificity of acetylcholine receptor in developing muscle. Studies with monoclonal antibodies." J Neuroimmunol 8(2-3): 159-66.

Stebbins, E. G. and D. Mochly-Rosen (2001). "Binding specificity for RACK1 resides in the V5 region of beta II protein kinase C." J Biol Chem 276(32): 29644-50.

Sweitzer, S. M., S. M. Wong, et al. (2004). "Exaggerated nociceptive responses on morphine withdrawal: roles of protein kinase C epsilon and gamma." Pain 110(1-2): 281-9.

Sweitzer, S. M., S. M. Wong, et al. (2004). "Protein kinase C epsilon and gamma: involvement in formalin-induced nociception in neonatal rats." J Pharmacol Exp Ther 309(2): 616-25.

Tabakoff, B., E. Nelson, et al. (2001). "Phosphorylation cascades control the actions of ethanol on cell cAMP signalling." J Biomed Sci 8(1): 44-51.

Tanaka, M., R. D. Terry, et al. (2004). "Suppression of graft coronary artery disease by a brief treatment with a selective epsilonPKC activator and a deltaPKC inhibitor in murine cardiac allografts." Circulation 110(11 Suppl 1): II194-9.

Tarrab-Hazdai, R., Y. Schmidt-Sole, et al. (1980). "Modification of acetylcholine receptor: chemical and immunological characterization of polyalanyl acetylcholine receptor." FEBS Lett 118(1): 35-8.

Wang, J., R. Bright, et al. (2004). "Cell-specific role for epsilon- and beta1-protein kinase C isozymes in protecting cortical neurons and astrocytes from ischemia-like injury." Neuropharmacology 47(1): 136-45.

Theodore et al., *J. Neurosci.*, 15:7158-7167 (1995).

Uemura, S., et al., *Circulation*, 88:1291-1298, (2001).

Vives et al., *J. Biol. Chem*, 272:16010-16017 (1997).

Way, K.J., et al., *TIPS*, 21(5):181-187 (2000).

Way, K. J., E. Chou, et al. (2000). "Identification of PKC-isoform-specific biological actions using pharmacological approaches." Trends Pharmacol Sci 21(5): 181-7.

Xiao, G. Q., D. Mochly-Rosen, et al. (2003). "PKC isozyme selective regulation of cloned human cardiac delayed slow rectifier K current." Biochem Biophys Res Commun 306(4): 1019-25.

Xiao, G. Q., Y. Qu, et al. (2001). "Evidence for functional role of epsilonPKC isozyme in the regulation of cardiac Na(+) channels." Am J Physiol Cell Physiol 281(5): C1477-86.

Yedovitzky, M., D. Mochly-Rosen, et al. (1997). "Translocation inhibitors define specificity of protein kinase C isoenzymes in pancreatic beta-cells." J Biol Chem 272(3): 1417-20.

Yoshida et al., *Biochimica et Biophysica ACTA*, 14:230-238 (1999).

Zhang, Z. H., J. A. Johnson, et al. (1997). "C2 region-derived peptides of beta-protein kinase C regulate cardiac Ca2+ channels." Circ Res 80(5): 720-9.

Zhou, L. Y., M. Disatnik, et al. (1996). "Differential activation of protein kinase C isozymes by phorbol ester and collagen in human skin microvascular endothelial cells." J Invest Dermatol 107(2): 248-52.

\* cited by examiner

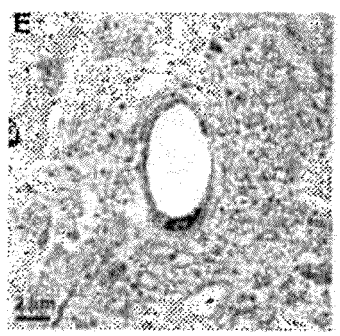 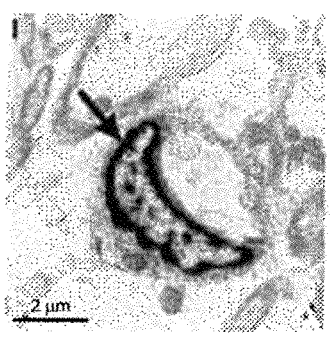 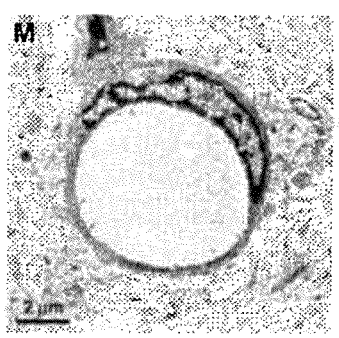
Fig. 4G   Fig. 4H   Fig. 4I
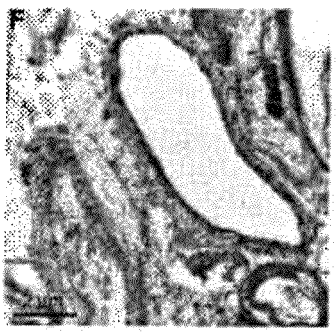 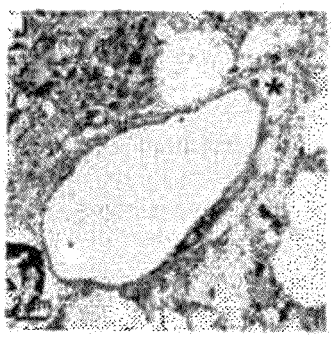 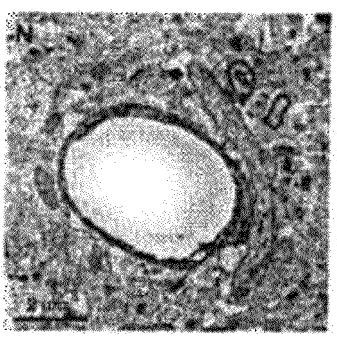
Fig. 4J   Fig. 4K   Fig. 4L

SEQUENCE LISTING

<160> NUMBER OF SEQ ID NOS: 85

<210> SEQ ID NO 1
<211> LENGTH: 10
<212> TYPE: PRT
<213> ORGANISM: Rattus norvegicus

<400> SEQUENCE: 1

Ser Phe Asn Ser Tyr Glu Leu Gly Ser Leu
1               5                   10

<210> SEQ ID NO 2
<211> LENGTH: 11
<212> TYPE: PRT
<213> ORGANISM: Rattus norvegicus

<400> SEQUENCE: 2

Ala Leu Thr Thr Asp Arg Gly Lys Thr Leu Val
1               5                   10

<210> SEQ ID NO 3
<211> LENGTH: 14
<212> TYPE: PRT
<213> ORGANISM: Rattus norvegicus

<400> SEQUENCE: 3

Lys Ala Glu Phe Trp Leu Asp Leu Gln Pro Gln Ala Lys Val
1               5                   10

<210> SEQ ID NO 4
<211> LENGTH: 58
<212> TYPE: PRT
<213> ORGANISM: Rattus norvegicus

<400> SEQUENCE: 4

Pro Phe Arg Pro Lys Val Lys Ser Pro Arg Pro Tyr Ser Asn Phe Asp
1               5                   10                  15

Gln Glu Phe Leu Asn Glu Lys Ala Arg Leu Ser Tyr Ser Asp Lys Asn
            20                  25                  30

Leu Ile Asp Ser Met Asp Gln Ser Ala Phe Ala Gly Phe Ser Phe Val
        35                  40                  45

Asn Pro Lys Phe Glu His Leu Leu Glu Asp
    50                  55

<210> SEQ ID NO 5
<211> LENGTH: 10
<212> TYPE: PRT
<213> ORGANISM: Artificial Sequence
<220> FEATURE:
<223> OTHER INFORMATION: synthetic variant

<400> SEQUENCE: 5

Thr Phe Asn Ser Tyr Glu Leu Gly Ser Leu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthetic variant

<400> SEQUENCE: 6

Ala Phe Asn Ser Tyr Glu Leu Gly Ser Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic variant

<400> SEQUENCE: 7

```
Ser Phe Asn Ser Tyr Glu Leu Gly Thr Leu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: synthetic variant

<400> SEQUENCE: 8

Thr Phe Asn Ser Tyr Glu Leu Gly Thr Leu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: synthetic variant

<400> SEQUENCE: 9

Ser Tyr Asn Ser Tyr Glu Leu Gly Ser Leu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: synthetic variant

<400> SEQUENCE: 10

Ser Phe Asn Ser Phe Glu Leu Gly Ser Leu
1               5                   10

<210> SEQ ID NO 11
<211> LENGTH: 9
<212> TYPE: PRT
<213> ORGANISM: Artificial Sequence
<220> FEATURE:
<223> OTHER INFORMATION: synthetic variant

<400> SEQUENCE: 11

Ser Asn Ser Tyr Asp Leu Gly Ser Leu
1               5

<210> SEQ ID NO 12
<211> LENGTH: 10
<212> TYPE: PRT
<213> ORGANISM: Artificial Sequence
<220> FEATURE:
<223> OTHER INFORMATION: synthetic variant

<400> SEQUENCE: 12

Ser Phe Asn Ser Tyr Glu Leu Pro Ser Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: synthetic variant

<400> SEQUENCE: 13

Ser Phe Asn Ser Tyr Glu Ile Gly Ser Val
```

<210> SEQ ID NO 14
<211> LENGTH: 10
<212> TYPE: PRT
<213> ORGANISM: Artificial Sequence
<220> FEATURE:
<223> OTHER INFORMATION: synthetic variant

<400> SEQUENCE: 14

Ser Phe Asn Ser Tyr Glu Val Gly Ser Ile
1               5                   10

<210> SEQ ID NO 15
<211> LENGTH: 10
<212> TYPE: PRT
<213> ORGANISM: Artificial Sequence
<220> FEATURE:
<223> OTHER INFORMATION: synthetic variant

<400> SEQUENCE: 15

Ser Phe Asn Ser Tyr Glu Leu Gly Ser Val
1               5                   10

<210> SEQ ID NO 16
<211> LENGTH: 10
<212> TYPE: PRT
<213> ORGANISM: Artificial Sequence
<220> FEATURE:
<223> OTHER INFORMATION: synthetic variant

<400> SEQUENCE: 16

Ser Phe Asn Ser Tyr Glu Leu Gly Ser Ile
1               5                   10

<210> SEQ ID NO 17
<211> LENGTH: 10
<212> TYPE: PRT
<213> ORGANISM: Artificial Sequence
<220> FEATURE:
<223> OTHER INFORMATION: synthetic variant

<400> SEQUENCE: 17

Ser Phe Asn Ser Tyr Glu Ile Gly Ser Leu
1               5                   10

<210> SEQ ID NO 18
<211> LENGTH: 10
<212> TYPE: PRT
<213> ORGANISM: Artificial Sequence
<220> FEATURE:
<223> OTHER INFORMATION: synthetic variant

<400> SEQUENCE: 18

Ser Phe Asn Ser Tyr Glu Val Gly Ser Leu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: synthetic variant

<400> SEQUENCE: 19

Ala Phe Asn Ser Tyr Glu Leu Gly Ser Leu
1               5                   10

```
<210> SEQ ID NO 20
<211> LENGTH: 6
<212> TYPE: PRT
<213> ORGANISM: Rattus norvegicus

<400> SEQUENCE: 20

Tyr Glu Leu Gly Ser Leu
1               5

<210> SEQ ID NO 21
<211> LENGTH: 6
<212> TYPE: PRT
<213> ORGANISM: Artificial Sequence
<220> FEATURE:
<223> OTHER INFORMATION: synthetic variant

<400> SEQUENCE: 21

Tyr Asp Leu Gly Ser Leu
1               5

<210> SEQ ID NO 22
<211> LENGTH: 6
<212> TYPE: PRT
<213> ORGANISM: Artificial Sequence
<220> FEATURE:
<223> OTHER INFORMATION: synthetic variant

<400> SEQUENCE: 22

Phe Asp Leu Gly Ser Leu
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic variant

<400> SEQUENCE: 23

Tyr Asp Ile Gly Ser Leu
1               5

<210> SEQ ID NO 24
<211> LENGTH: 4
<212> TYPE: PRT
<213> ORGANISM: Artificial Sequence
<220> FEATURE:
<223> OTHER INFORMATION: synthetic variant

<400> SEQUENCE: 24

Ile Gly Ser Leu
1

<210> SEQ ID NO 25
<211> LENGTH: 6
<212> TYPE: PRT
<213> ORGANISM: Artificial Sequence
<220> FEATURE:
<223> OTHER INFORMATION: synthetic variant

<400> SEQUENCE: 25

Tyr Asp Val Gly Ser Leu
1               5

<210> SEQ ID NO 26
<211> LENGTH: 6
<212> TYPE: PRT
```

```
<213> ORGANISM: Artificial Sequence
<220> FEATURE:
<223> OTHER INFORMATION: synthetic variant

<400> SEQUENCE: 26

Tyr Asp Leu Pro Ser Leu
1               5

<210> SEQ ID NO 27
<211> LENGTH: 6
<212> TYPE: PRT
<213> ORGANISM: Artificial Sequence
<220> FEATURE:
<223> OTHER INFORMATION: synthetic variant

<400> SEQUENCE: 27

Tyr Asp Leu Gly Ile Leu
1               5

<210> SEQ ID NO 28
<211> LENGTH: 6
<212> TYPE: PRT
<213> ORGANISM: Artificial Sequence
<220> FEATURE:
<223> OTHER INFORMATION: synthetic variant

<400> SEQUENCE: 28

Tyr Asp Leu Gly Ser Ile
1               5

<210> SEQ ID NO 29
<211> LENGTH: 6
<212> TYPE: PRT
<213> ORGANISM: Artificial Sequence
<220> FEATURE:
<223> OTHER INFORMATION: synthetic variant

<400> SEQUENCE: 29

Tyr Asp Leu Gly Ser Val
1               5

<210> SEQ ID NO 30
<211> LENGTH: 4
<212> TYPE: PRT
<213> ORGANISM: Rattus norvegicus

<400> SEQUENCE: 30

Leu Gly Ser Leu
1

<210> SEQ ID NO 31
<211> LENGTH: 4
<212> TYPE: PRT
<213> ORGANISM: Artificial Sequence
<220> FEATURE:
<223> OTHER INFORMATION: synthetic variant

<400> SEQUENCE: 31

Ile Gly Ser Leu
1

<210> SEQ ID NO 32
<211> LENGTH: 4
<212> TYPE: PRT
<213> ORGANISM: Artificial Sequence
<220> FEATURE:
<223> OTHER INFORMATION: synthetic variant
```

```
<400> SEQUENCE: 32

Val Gly Ser Leu
1

<210> SEQ ID NO 33
<211> LENGTH: 4
<212> TYPE: PRT
<213> ORGANISM: Artificial Sequence
<220> FEATURE:
<223> OTHER INFORMATION: synthetic variant

<400> SEQUENCE: 33

Leu Pro Ser Leu
1

<210> SEQ ID NO 34
<211> LENGTH: 4
<212> TYPE: PRT
<213> ORGANISM: Artificial Sequence
<220> FEATURE:
<223> OTHER INFORMATION: synthetic variant

<400> SEQUENCE: 34

Leu Gly Ile Leu
1

<210> SEQ ID NO 35
<211> LENGTH: 4
<212> TYPE: PRT
<213> ORGANISM: Artificial Sequence
<220> FEATURE:
<223> OTHER INFORMATION: synthetic variant

<400> SEQUENCE: 35

Leu Gly Ser Ile
1

<210> SEQ ID NO 36
<211> LENGTH: 4
<212> TYPE: PRT
<213> ORGANISM: Artificial Sequence
<220> FEATURE:
<223> OTHER INFORMATION: synthetic variant

<400> SEQUENCE: 36

Leu Gly Ser Val
1

<210> SEQ ID NO 37
<211> LENGTH: 11
<212> TYPE: PRT
<213> ORGANISM: Artificial Sequence
<220> FEATURE:
<223> OTHER INFORMATION: synthetic variant

<400> SEQUENCE: 37

Ala Leu Ser Thr Asp Arg Gly Lys Thr Leu Val
1               5                   10

<210> SEQ ID NO 38
<211> LENGTH: 11
<212> TYPE: PRT
<213> ORGANISM: Artificial Sequence
<220> FEATURE:
<223> OTHER INFORMATION: synthetic variant

<400> SEQUENCE: 38
```

```
Ala Leu Thr Ser Asp Arg Gly Lys Thr Leu Val
1               5                   10

<210> SEQ ID NO 39
<211> LENGTH: 11
<212> TYPE: PRT
<213> ORGANISM: Artificial Sequence
<220> FEATURE:
<223> OTHER INFORMATION: synthetic variant

<400> SEQUENCE: 39

Ala Leu Thr Thr Asp Arg Gly Lys Ser Leu Val
1               5                   10

<210> SEQ ID NO 40
<211> LENGTH: 11
<212> TYPE: PRT
<213> ORGANISM: Artificial Sequence
<220> FEATURE:
<223> OTHER INFORMATION: synthetic variant

<400> SEQUENCE: 40

Ala Leu Thr Thr Asp Arg Pro Lys Thr Leu Val
1               5                   10

<210> SEQ ID NO 41
<211> LENGTH: 11
<212> TYPE: PRT
<213> ORGANISM: Artificial Sequence
<220> FEATURE:
<223> OTHER INFORMATION: synthetic variant

<400> SEQUENCE: 41

Ala Leu Thr Thr Asp Arg Gly Arg Thr Leu Val
1               5                   10

<210> SEQ ID NO 42
<211> LENGTH: 11
<212> TYPE: PRT
<213> ORGANISM: Artificial Sequence
<220> FEATURE:
<223> OTHER INFORMATION: synthetic variant

<400> SEQUENCE: 42

Ala Leu Thr Thr Asp Lys Gly Lys Thr Leu Val
1               5                   10

<210> SEQ ID NO 43
<211> LENGTH: 11
<212> TYPE: PRT
<213> ORGANISM: Artificial Sequence
<220> FEATURE:
<223> OTHER INFORMATION: synthetic variant

<400> SEQUENCE: 43

Ala Leu Thr Thr Asp Lys Gly Lys Thr Leu Val
1               5                   10

<210> SEQ ID NO 44
<211> LENGTH: 14
<212> TYPE: PRT
<213> ORGANISM: Artificial Sequence
<220> FEATURE:
<223> OTHER INFORMATION: synthetic variant

<400> SEQUENCE: 44

Arg Ala Glu Phe Trp Leu Asp Leu Gln Pro Gln Ala Lys Val
1               5                   10
```

```
<210> SEQ ID NO 45
<211> LENGTH: 14
<212> TYPE: PRT
<213> ORGANISM: Artificial Sequence
<220> FEATURE:
<223> OTHER INFORMATION: synthetic variant

<400> SEQUENCE: 45

Lys Ala Asp Phe Trp Leu Asp Leu Gln Pro Gln Ala Lys Val
1               5                   10

<210> SEQ ID NO 46
<211> LENGTH: 14
<212> TYPE: PRT
<213> ORGANISM: Artificial Sequence
<220> FEATURE:
<223> OTHER INFORMATION: synthetic variant

<400> SEQUENCE: 46

Lys Ala Glu Phe Trp Leu Glu Leu Gln Pro Gln Ala Lys Val
1               5                   10

<210> SEQ ID NO 47
<211> LENGTH: 14
<212> TYPE: PRT
<213> ORGANISM: Artificial Sequence
<220> FEATURE:
<223> OTHER INFORMATION: synthetic variant

<400> SEQUENCE: 47

Lys Ala Glu Phe Trp Leu Asp Leu Gln Pro Gln Ala Arg Val
1               5                   10

<210> SEQ ID NO 48
<211> LENGTH: 14
<212> TYPE: PRT
<213> ORGANISM: Artificial Sequence
<220> FEATURE:
<223> OTHER INFORMATION: synthetic variant

<400> SEQUENCE: 48

Lys Ala Glu Tyr Trp Leu Asp Leu Gln Pro Gln Ala Lys Val
1               5                   10

<210> SEQ ID NO 49
<211> LENGTH: 14
<212> TYPE: PRT
<213> ORGANISM: Artificial Sequence
<220> FEATURE:
<223> OTHER INFORMATION: synthetic variant

<400> SEQUENCE: 49

Lys Ala Glu Phe Trp Ile Asp Leu Gln Pro Gln Ala Lys Val
1               5                   10

<210> SEQ ID NO 50
<211> LENGTH: 14
<212> TYPE: PRT
<213> ORGANISM: Artificial Sequence
<220> FEATURE:
<223> OTHER INFORMATION: synthetic variant

<400> SEQUENCE: 50

Lys Ala Glu Phe Trp Val Asp Leu Gln Pro Gln Ala Lys Val
1               5                   10
```

```
<210> SEQ ID NO 51
<211> LENGTH: 14
<212> TYPE: PRT
<213> ORGANISM: Artificial Sequence
<220> FEATURE:
<223> OTHER INFORMATION: synthetic variant

<400> SEQUENCE: 51

Lys Ala Glu Phe Trp Leu Asp Ile Gln Pro Gln Ala Lys Val
1               5                   10

<210> SEQ ID NO 52
<211> LENGTH: 14
<212> TYPE: PRT
<213> ORGANISM: Artificial Sequence
<220> FEATURE:
<223> OTHER INFORMATION: synthetic variant

<400> SEQUENCE: 52

Lys Ala Glu Phe Trp Leu Asp Val Gln Pro Gln Ala Lys Val
1               5                   10

<210> SEQ ID NO 53
<211> LENGTH: 14
<212> TYPE: PRT
<213> ORGANISM: Artificial Sequence
<220> FEATURE:
<223> OTHER INFORMATION: synthetic variant

<400> SEQUENCE: 53

Lys Ala Glu Phe Trp Leu Asp Leu Asn Pro Gln Ala Lys Val
1               5                   10

<210> SEQ ID NO 54
<211> LENGTH: 14
<212> TYPE: PRT
<213> ORGANISM: Artificial Sequence
<220> FEATURE:
<223> OTHER INFORMATION: synthetic variant

<400> SEQUENCE: 54

Lys Ala Glu Phe Trp Leu Asp Leu Gln Pro Asn Ala Lys Val
1               5                   10

<210> SEQ ID NO 55
<211> LENGTH: 14
<212> TYPE: PRT
<213> ORGANISM: Artificial Sequence
<220> FEATURE:
<223> OTHER INFORMATION: synthetic variant

<400> SEQUENCE: 55

Lys Ala Glu Phe Trp Leu Asp Leu Gln Pro Gln Ala Lys Ile
1               5                   10

<210> SEQ ID NO 56
<211> LENGTH: 14
<212> TYPE: PRT
<213> ORGANISM: Artificial Sequence
<220> FEATURE:
<223> OTHER INFORMATION: synthetic variant

<400> SEQUENCE: 56

Lys Ala Glu Phe Trp Leu Asp Leu Gln Pro Gln Ala Lys Leu
1               5                   10

<210> SEQ ID NO 57
<211> LENGTH: 14
```

```
<212> TYPE: PRT
<213> ORGANISM: Artificial Sequence
<220> FEATURE:
<223> OTHER INFORMATION: synthetic variant

<400> SEQUENCE: 57

Lys Ala Glu Phe Trp Ala Asp Leu Gln Pro Gln Ala Lys Val
1               5                   10

<210> SEQ ID NO 58
<211> LENGTH: 14
<212> TYPE: PRT
<213> ORGANISM: Artificial Sequence
<220> FEATURE:
<223> OTHER INFORMATION: synthetic variant

<400> SEQUENCE: 58

Lys Ala Glu Phe Trp Leu Asp Ala Gln Pro Gln Ala Lys Val
1               5                   10

<210> SEQ ID NO 59
<211> LENGTH: 14
<212> TYPE: PRT
<213> ORGANISM: Artificial Sequence
<220> FEATURE:
<223> OTHER INFORMATION: synthetic variant

<400> SEQUENCE: 59

Lys Ala Glu Phe Trp Leu Asp Leu Gln Pro Gln Ala Lys Ala
1               5                   10

<210> SEQ ID NO 60
<211> LENGTH: 7
<212> TYPE: PRT
<213> ORGANISM: Rattus norvegicus

<400> SEQUENCE: 60

Lys Ala Glu Phe Trp Leu Asp
1               5

<210> SEQ ID NO 61
<211> LENGTH: 8
<212> TYPE: PRT
<213> ORGANISM: Rattus norvegicus

<400> SEQUENCE: 61

Asp Leu Gln Pro Gln Ala Lys Val
1               5

<210> SEQ ID NO 62
<211> LENGTH: 8
<212> TYPE: PRT
<213> ORGANISM: Rattus norvegicus

<400> SEQUENCE: 62

Glu Phe Trp Leu Asp Leu Gln Pro
1               5

<210> SEQ ID NO 63
<211> LENGTH: 7
<212> TYPE: PRT
<213> ORGANISM: Rattus norvegicus

<400> SEQUENCE: 63

Leu Asp Leu Gln Pro Gln Ala
1               5
```

<210> SEQ ID NO 64
<211> LENGTH: 7
<212> TYPE: PRT
<213> ORGANISM: Rattus norvegicus

<400> SEQUENCE: 64

Leu Gln Pro Gln Ala Lys Val
1               5

<210> SEQ ID NO 65
<211> LENGTH: 7
<212> TYPE: PRT
<213> ORGANISM: Rattus norvegicus

<400> SEQUENCE: 65

Ala Glu Phe Trp Leu Asp Leu
1               5

<210> SEQ ID NO 66
<211> LENGTH: 7
<212> TYPE: PRT
<213> ORGANISM: Rattus norvegicus

<400> SEQUENCE: 66

Trp Leu Asp Leu Gln Pro Gln
1               5

<210> SEQ ID NO 67
<211> LENGTH: 8
<212> TYPE: PRT
<213> ORGANISM: Rattus norvegicus

<400> SEQUENCE: 67

Ser Pro Arg Pro Tyr Ser Asn Phe
1               5

<210> SEQ ID NO 68
<211> LENGTH: 8
<212> TYPE: PRT
<213> ORGANISM: Rattus norvegicus

<400> SEQUENCE: 68

Arg Pro Tyr Ser Asn Phe Asp Gln
1               5

<210> SEQ ID NO 69
<211> LENGTH: 8
<212> TYPE: PRT
<213> ORGANISM: Rattus norvegicus

<400> SEQUENCE: 69

Ser Asn Phe Asp Gln Glu Phe Leu
1               5

<210> SEQ ID NO 70
<211> LENGTH: 8
<212> TYPE: PRT
<213> ORGANISM: Rattus norvegicus

<400> SEQUENCE: 70

Asp Gln Glu Phe Leu Asn Glu Lys
1               5

<210> SEQ ID NO 71
<211> LENGTH: 8

```
<212> TYPE: PRT
<213> ORGANISM: Rattus norvegicus

<400> SEQUENCE: 71

Phe Leu Asn Glu Lys Ala Arg Leu
1               5

<210> SEQ ID NO 72
<211> LENGTH: 8
<212> TYPE: PRT
<213> ORGANISM: Rattus norvegicus

<400> SEQUENCE: 72

Leu Ile Asp Ser Met Asp Gln Ser
1               5

<210> SEQ ID NO 73
<211> LENGTH: 8
<212> TYPE: PRT
<213> ORGANISM: Rattus norvegicus

<400> SEQUENCE: 73

Ser Met Asp Gln Ser Ala Phe Ala
1               5

<210> SEQ ID NO 74
<211> LENGTH: 8
<212> TYPE: PRT
<213> ORGANISM: Rattus norvegicus

<400> SEQUENCE: 74

Asp Gln Ser Ala Phe Ala Gly Phe
1               5

<210> SEQ ID NO 75
<211> LENGTH: 8
<212> TYPE: PRT
<213> ORGANISM: Rattus norvegicus

<400> SEQUENCE: 75

Phe Val Asn Pro Lys Phe Glu His
1               5

<210> SEQ ID NO 76
<211> LENGTH: 8
<212> TYPE: PRT
<213> ORGANISM: Rattus norvegicus

<400> SEQUENCE: 76

Lys Phe Glu His Leu Leu Glu Asp
1               5

<210> SEQ ID NO 77
<211> LENGTH: 8
<212> TYPE: PRT
<213> ORGANISM: Rattus norvegicus

<400> SEQUENCE: 77

Asn Glu Lys Ala Arg Leu Ser Tyr
1               5

<210> SEQ ID NO 78
<211> LENGTH: 8
<212> TYPE: PRT
<213> ORGANISM: Rattus norvegicus
```

-continued

```
<400> SEQUENCE: 78

Arg Leu Ser Tyr Ser Asp Lys Asn
1               5

<210> SEQ ID NO 79
<211> LENGTH: 8
<212> TYPE: PRT
<213> ORGANISM: Rattus norvegicus

<400> SEQUENCE: 79

Ser Tyr Ser Asp Lys Asn Leu Ile
1               5

<210> SEQ ID NO 80
<211> LENGTH: 8
<212> TYPE: PRT
<213> ORGANISM: Rattus norvegicus

<400> SEQUENCE: 80

Asp Lys Asn Leu Ile Asp Ser Met
1               5

<210> SEQ ID NO 81
<211> LENGTH: 8
<212> TYPE: PRT
<213> ORGANISM: Rattus norvegicus

<400> SEQUENCE: 81

Pro Phe Arg Pro Lys Val Lys Ser
1               5

<210> SEQ ID NO 82
<211> LENGTH: 8
<212> TYPE: PRT
<213> ORGANISM: Rattus norvegicus

<400> SEQUENCE: 82

Arg Pro Lys Val Lys Ser Pro Arg
1               5

<210> SEQ ID NO 83
<211> LENGTH: 8
<212> TYPE: PRT
<213> ORGANISM: Rattus norvegicus

<400> SEQUENCE: 83

Val Lys Ser Pro Arg Pro Tyr Ser
1               5

<210> SEQ ID NO 84
<211> LENGTH: 17
<212> TYPE: PRT
<213> ORGANISM: Drosophila sp.

<400> SEQUENCE: 84

Cys Arg Gln Ile Lys Ile Trp Phe Gln Asn Arg Arg Met Lys Trp Lys
1               5                   10                  15

Lys

<210> SEQ ID NO 85
<211> LENGTH: 11
<212> TYPE: PRT
<213> ORGANISM: Human Immunodeficiency Virus 1

<400> SEQUENCE: 85
```

```
Tyr Gly Arg Lys Lys Arg Arg Gln Arg Arg
1               5                   10
```

METHODS OF INCREASING CEREBRAL BLOOD FLOW

CROSS-REFERENCE TO RELATED APPLICATIONS

This application is a continuation of application Ser. No. 11/317,806, filed Dec. 23, 2005, now U.S. Pat. No. 7,563,772, which claims the benefit of U.S. Provisional Application No. 60/641,413, filed Jan. 4, 2005. Both documents are incorporated herein by reference in their entirety.

STATEMENT REGARDING FEDERALLY SPONSORED RESEARCH

This work was supported in part by the National Institutes of Health under grant number NS44350. Accordingly, the United States Government has certain rights in the invention.

REFERENCE TO SEQUENCE LISTING, TABLE OR COMPUTER PROGRAM

A Sequence Listing is being submitted electronically via EFS in the form of a text file, created 22 Jun. 2009, and named "586008214US01seqlist.txt" (4,584), the contents of which are incorporated herein by reference in their entirety.

TECHNICAL FIELD

The subject matter described herein relates to methods of increasing cerebral blood flow in a vessel experiencing decreased blood flow. More specifically, the subject matter relates to methods of increasing cerebral blood flow in a blood vessel by administering an inhibitor of delta protein kinase C (δPKC).

BACKGROUND

An ischemic stroke occurs when the flow of blood to the brain is obstructed. Cerebral ischemia and reperfusion injury, due to diseases such as stroke and cardiac arrest, are a leading cause of disability and death in the US. Over 700,000 strokes occur annually in the United States (U.S.) alone, and, as of 2001, 4,800,000 people were living with the consequences of stroke. The overall death rate for stroke is approximately 58%, with approximately 50% of these patients dying in a hospital (American Heart Association Heart Disease and Stroke Statistics, 2004 Update).

In addition to ischemic stroke, hemorrhagic stroke (including intracerebral and subarachnoid types) account for 12% of all stroke incidents. Unlike ischemic strokes, hemorrhagic stroke is due to loss of blood from the vascular system into the parenchymal, subarachnoid or subdural space. This type of stroke incurs a much higher mortality rate (37-38% mortality within 30 days) in comparison to ischemic stroke. (American Heart Association Heart Disease and Stroke Statistics, 2004 Update). Hemorrhagic stroke often leads to the production of chronic delayed cerebral vasoconstriction and vasospasm. In fact, ⅔ of patients which have been treated for subarachnoid hemorrhage suffer from cerebral vasospasm between days 3 and 13 after hemorrhage. Suhardja, A., *Nature Clin. Prac., Cardiovasc. Med.* 1(2):110-116 (2004). These alterations in cerebral vascular function occur both in larger diameter vessels (e.g., basilar artery, middle cerebral artery), and in smaller diameter vessels, including capillaries and arterioles. Vasospasm is due in part to build up of reactive blood products surrounding the vasculature, including oxyhemoglobin, which sequesters the vasodilator nitric oxide (NO). Loss of cerebral blood flow autoregulation, including vasoconstriction and vasospasm, lead to increased cerebral damage from restricted blood flow, causing worsening of brain damage in the area surrounding the trauma, and accounting in part for the worsened outcome of hemorrhagic stroke patients.

Other causes of compromised cerebral vascular autoregulation include chronic high blood pressure, or hypertension. Hypertension affects approximately 1 in 5 Americans (1 in 4 adults) (American Heart Association Heart Disease and Stroke Statistics, 2004 Update) and is a significant risk factor for cerebral stroke injury, in addition to other chronic diseases including congestive heart failure. Hypertension has been correlated with reduced cerebral blood flow (Rodriguez, G., et al., *Stroke* 18(1):13-20 (1987)). Therefore, maintaining adequate cerebral perfusion is critical in managing cerebral protection in these at-risk patients. Control of cerebral blood flow is also important for maintaining brain perfusion in other idiopathic causes of cerebral vasoconstriction and vasospasm, including migraine, pregnancy, Call-Fleming syndrome and benign angiopathy of the central nervous system (Singhal, A. B. *Top. Stroke Rehabil.* 11(2),1-6 (2004)).

Additionally, the cost of cerebrovascular disease is enormous. Both from direct health expenditures and lost productivity due to morbidity and mortality, the cost of stroke in the U.S. amounts to approximately $53.6 billion. (American Heart Association Heart Disease and Stroke Statistics, 2004 Update).

Despite this large clinical need, current treatment options for cerebral ischemic and reperfusion injury are limited. The only clinically approved medication for stroke, recombinant tissue plasminogen activator (rtPA), is only used in about 1% to about 2% of patients nationally, due in large part to a short therapeutic window and high risk profile, including increased risk of cerebral hemorrhage and death.

In designing a drug or treatment for ischemic stroke, it is desirable to design a drug or treatment that may be administered multiple times without causing patient desensitization. Desensitization of patients to a drug occurs when the drug is administered and either has no therapeutic effect or the therapeutic effect decreases as a function of the number of times that the drug is administered. This occurs with several medications, including, for example, nitroglycerine used to treat cardiac ischemia.

There is therefore a need for a drug or treatment method for increasing blood flow in the blood vessels of the brain. There is further a need for such a drug or treatment method that does not cause patient desensitization, and therefore may allow chronic administration as needed. The present invention addresses these needs.

SUMMARY

It has been discovered that an inhibitor of delta protein kinase C (δPKC) can increase cerebral blood flow in a mammal experiencing decreased cerebral blood flow due to an ischemic or other hypoxic event. Accordingly, methods for increasing blood flow in such a mammalian brain blood vessel experiencing decreased blood flow are provided. Furthermore, methods for increasing blood flow in such a mammalian blood vessel that do not cause desensitization are provided. Kits for increasing blood flow in such a mammalian brain blood vessel are also provided.

In a first aspect of the invention, methods for increasing blood flow in a mammalian brain blood vessel characterized by, or otherwise experiencing, decreased blood flow due to a disease or condition, such as an ischemic event, are provided.

In one form, a method for increasing blood flow in such a mammalian brain blood vessel includes administering to a patient in need thereof a therapeutically effective amount of an inhibitor of δ protein kinase C. In certain forms of the invention, the inhibitor is a peptide, and is further a δV1-1 peptide. In alternate forms of the invention, the inhibitor is a δV1-2 peptide, a δV1-5 peptide or a δV5 peptide. Fragments or derivatives of the aforementioned peptides that may advantageously be used in the methods of the invention are further described. The methods may advantageously be used to effectively increase cerebral blood flow in conditions characterized by decreased cerebral blood flow. For example, the methods may be used to increase cerebral blood flow, and to thereby reduce injury, from an ischemic event, such as an ischemic stroke or from vasoconstriction or vasospasms following a hemorrhagic stroke. The methods may also be utilized to increase blood flow in a brain blood vessel in vivo for any other purpose where increased blood flow is desired, including in individuals experiencing decreased blood flow in one or more vessels due to chronic high blood pressure and/or due to idiopathic causes.

In one form of the invention, a method for increasing blood flow in a mammalian brain blood vessel characterized by, or otherwise experiencing, decreased blood flow due to a disease or condition described herein, or otherwise known in the art, includes administering to a patient in need thereof a therapeutically effective amount of an inhibitor of δ protein kinase C wherein the inhibitor is capable of chronic administration without causing patient desensitization to the inhibitor.

In yet other forms of the invention, a method for increasing blood flow in a mammalian brain blood vessel characterized by, or otherwise experiencing, decreased blood flow due to a disease or condition described herein and/or otherwise known in the art includes administering to a patient in need thereof a therapeutically effective amount of an inhibitor of δ protein kinase C multiple times without causing desensitization to the inhibitor.

In a second aspect of the invention, kits for increasing blood flow in a mammalian brain blood vessel characterized by, or otherwise experiencing, decreased blood flow due to a disease or condition described herein and/or otherwise known to the art are provided. In one form, a kit includes an inhibitor of δ protein kinase C as described herein and instructions for using the inhibitor to increase blood flow in one or more cerebral blood vessels.

It is an object of the invention to provide methods for increasing blood flow in a mammalian brain blood vessel characterized by, or otherwise experiencing, decreased blood flow due to a disease or condition, such as, for example, an ischemic event or vasoconstriction or vasospasm following a hemorrhagic stroke; due to chronic high blood pressure; and/or due to idiopathic causes.

It is a further object of the invention to provide methods for increasing blood flow in a mammalian brain blood vessel characterized by, or otherwise experiencing, decreased blood flow due to a disease or condition described herein and/or otherwise known to the art that do not cause patient desensitization to the drug effect.

It is yet another object of the invention to provide kits for increasing blood flow in a mammalian brain blood vessel characterized by, or otherwise experiencing, decreased blood flow due to a disease or condition described herein and/or otherwise known to the art.

In addition to the exemplary aspects and embodiments described above, further aspects and embodiments will become apparent by reference to the drawings and by study of the following descriptions.

BRIEF DESCRIPTION OF THE FIGURES

FIGS. 4A-4L are computer-generated photomicrographs of brain tissue from control (healthy) rats not subjected to ischemic/reperfusion injury (FIGS. 4A, 4D, 4G, 4J) and from rats subjected to ischemic/reperfusion injury by middle cerebral artery (MCA) occlusion and treated with TAT peptide (FIGS. 4B, 4E, 4H, 4K) or with δV1-1-TAT (FIGS. 4C, 4F, 4I, 4L).

DETAILED DESCRIPTION

Figure 1:
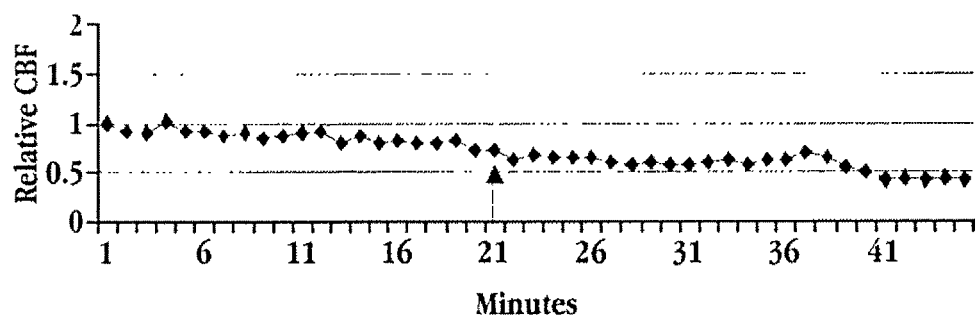
FIG. 1 shows a graph of cerebral blood flow (CBF) as a function of time in sham (non-stroked) rats treated with a therapeutic dosage of δV1-1 peptide as more fully described in Example 1. The arrow denotes delivery of δV1-1 peptide, Sham-treated rats were treated with the δV1-1 peptide and the CBF was measured, all as described in Example 1.

For the purposes of promoting an understanding of the subject matter described herein, reference will now be made to preferred embodiments and specific language will be used to describe the same. It will nevertheless be understood that no limitation of the scope is thereby intended, such alterations and further modifications of the subject matter, and such further applications of the principles illustrated herein, being contemplated as would normally occur to one skilled in the art to which the subject matter relates.

Methods of increasing blood flow in a vertebrate brain blood vessel characterized by, or otherwise experiencing, decreased blood flow due to a disease or condition are provided. The disease or condition is one that causes decreased cerebral blood flow. The decreased blood flow may arise from a variety of events, including an ischemic stroke, reperfusion, idiopathic causes or vasoconstriction or vasospasm 1) following or otherwise associated with a hemorrhagic stroke; 2) due to chronic high blood pressure; 3) due to reperfusion; and/or 4) due to idiopathic causes. It has been discovered that selected isozymes of protein kinase C (PKC) increase the flow of blood in such a mammalian brain blood vessel. It has also been discovered that such isozymes may be advantageously utilized to reduce cell, tissue or organ damage, death or other injury due to conditions characterized by decreased blood flow, including injury due to a hypoxic event, such as an ischemic stroke, or injury due to vasoconstriction or vasospasm following a hemorrhagic stroke; due to chronic high blood pressure; and/or due to idiopathic causes. By "hypoxic event" or "hypoxia", it is meant herein an event which causes a cell, tissue or organ to receive an inadequate supply of oxygen. "Ischemic stroke", "ischemia" or "ischemic event", as used herein refers to an insufficient supply of blood to a specific cell, tissue or organ. A consequence of decreased blood supply is an inadequate supply of oxygen (i.e., hypoxia) and nutrients to the cell, tissue or organ.

Although not being limited by theory, it is believed that during and/or after an ischemic event there exists a hypoperfused area of tissue known as the ischemic penumbra which surrounds the tissue directly fed from the occluded vessel, or is in brain areas outside the direct periphery of the ischemic core. Although some of this tissue area directly fed from the occluded vessel, known as the ischemic core, may be irreversibly damaged within minutes of the start of the ischemic event, it is believed herein that the penumbral tissue may be salvaged by maintaining blood flow and/or vessel patency.

A hypoperfused area can also occur in patients who have vasoconstriction following hemorrhagic stroke; due to chronic high blood pressure and/or due to idiopathic causes. It is believed herein that the hypoperfusion caused by the vasoconstriction induces neuronal, glial and vascular damage that may be salvaged by improving blood flow and/or vessel patency. In one form of the invention, a method includes administering to a patient in need thereof a therapeutically effective amount of an inhibitor of δ protein kinase C (δPKC).

It has also been discovered that the inhibitor of δPKC can be chronically administered without inducing desensitization to the inhibitor. Accordingly, in yet another form of the invention, a method of increasing blood flow in a vertebrate brain blood vessel characterized by, or otherwise experiencing, decreased blood flow due to a disease or condition described herein includes administering to a patient a therapeutically effective amount of an inhibitor of δPKC, wherein the inhibitor is capable of chronic administration without causing desensitization to the inhibitor. Kits for increasing blood flow in a mammalian brain blood vessel characterized by, or otherwise experiencing, decreased blood flow due to a disease or condition described herein are also provided. In one form, a kit includes an inhibitor of δPKC and instructions for using the inhibitor to increase blood flow in a vertebrate brain blood vessel experiencing decreased blood flow due to a disease or condition described herein.

In one aspect, methods of increasing blood flow in a vertebrate brain blood vessel characterized by, or otherwise experiencing, decreased blood flow due to a disease or condition are provided. In one embodiment, a method includes administering to a patient a therapeutically effective amount of an inhibitor of δPKC.

By "blood flow", it is meant generally herein the amount of blood flowing in the respective vessel per unit time, By "increasing blood flow", it is meant herein that the blood flow at a particular time is increased relative to the blood flow at some predetermined time point, such as during the onset of, or a specified time period after the onset of, an ischemic, hypoxic or other cell, tissue or organ injuring event described herein and/or known in the art; including when a patient is experiencing vasoconstriction or vasospasm due to a hemorrhagic stroke or while experiencing chronic high blood pressure. Blood flow is typically increased after treatment with the inhibitors described herein relative to the blood flow prior to such treatment. By "decreased blood flow" it is meant herein that the blood flow at a particular time is decreased relative to blood flow at some predetermined time point, such as prior to the onset of, or a specified time period after the onset of, an ischemic, hypoxic or other cell, tissue or organ injuring event described herein and/or known in the art; including when a patient is experiencing vasoconstriction or vasospasm due to, for example, a hemorrhagic stroke or while experiencing chronic high blood pressure. Several methods are known in the art for determining blood flow in one or more blood vessels. For example, Laser Doppler Flowmetry (LDF), Magnetic Resonance Imaging (MRI), Positron Emission Tomography (PET), and Computed Tomography (CT) Imaging, including Single Photon Emission Computed Tomography (SPECT) may be used to determine cerebral blood flow (Leenders, K. L., et al. *Brain* 113:27-47 (1990); Sakai, F., et al. *J. Cereb. Blood Flow Metab.* 5:207-213 (1988); Rempp, K. A., et al, *Radiology* 193:637-641 (1994); Baird, A. E. and Warach, S., *J. Cereb. Blood Flow Metab.* 18:583-609 (1998); Danus, G., et al., *Radiology* 213:141-149 (1999); Calamante, F., et al., *J. Cereb. Blood Flow Metab.* 19:701-735 (1999); Ginsberg, M. D., et al., *J. Cereb Blood Flow Metab.* 2(1):89-98 (1982); Fukuda, O., *Neurosurgery* 36(2):358-364 (1995); Perez-Pinzon, et al., *J. Neurolog. Sci.* 153 (1):25-31 (1997); Borlongan, et al., *Brain Res.* 1010(1-2):108-116 (2004)). It is realized that these and other known methods may involve different measurements and may not provide blood flow in terms of volume per unit time. For example, LDF provides a value for blood flow that is called the red blood cell flux, defined as the product of the number of red blood cells and their velocity. Blood flow as described herein may therefore be reported in a wide variety of formats and/or units.

A wide variety of inhibitors of δPKC may be utilized in the described method. By inhibitor of δPKC, it is meant herein a compound that inhibits the biological activity or function of δPKC. As known in the art, δPKC is involved a myriad of cellular processes, including regulation of cell growth, and regulation of gene expression. The inhibitors may, for example, inhibit the enzymatic activity of δPKC. The inhibitors may inhibit the activity of δPKC by, for example, preventing activation of δPKC or may prevent binding of δPKC to its protein substrate. Such an inhibition of enzymatic activity would prevent, for example, phosphorylation of amino acids in proteins. The inhibitor may also prevent binding of δPKC to its anchoring protein, also known as receptor for activated kinase (RACK) and the associated translocation of δPKC to its subcellular location.

In one form of the method, organic molecule inhibitors, including alkaloids, may be utilized. For example, benzophenanthridine alkaloids may be used, including chelerythrine, sanguirubine, chelirubine, sanguilutine, and chililutine. Such alkaloids can be purchased commercially and/or isolated from plants as known in the art and as described, for example, in U.S. Pat. No. 5,133,981.

The bisindolylmaleimide class of compounds may also be used as inhibitors of δPKC. Exemplary bisindolylmaleimides include bisindolylmaleimide I, bisindolylmaleimide II, bisindolylmaleimide III, bisindolylmaleimide IV, bisindolylmaleimide V, bisindolylmaleimide VI, bisindolylmaleimide VI, bisindolylmaleimide VIII, bisindolylmaleimide IX, bisindolylmaleimide X and other bisindolylmaleimides that are effective in inhibiting δPKC. Such compounds may be purchased commercially and/or synthesized by methods known to the skilled artisan and as described, for example, in U.S. Pat. No. 5,559,228 and Brenner, et al., *Tetrahedron* 44(10) 2887-2892 (1988). Anti-helminthic dyes obtained from the kamala tree and effective in inhibiting δPKC may also be utilized, including rottlerin, and may be purchased commercially or synthesized by the skilled artisan.

In certain forms of the method, a protein inhibitor of δPKC may be utilized. The protein inhibitor may be in the form of a peptide. Protein, peptide and polypeptide as used herein and as known in the art refer to a compound made up of a chain of amino acid monomers linked by peptide bonds. Unless otherwise stated, the individual sequence of the peptide is given in the order from the amino terminus to the carboxyl terminus. The protein inhibitor of δPKC may be obtained by methods known to the skilled artisan. For example, the protein inhibitor may be chemically synthesized using various solid phase synthetic technologies known to the art and as described, for example, in Williams, Paul Lloyd, et al. *Chemical Approaches to the Synthesis of Peptides and Proteins*, CRC Press, Boca Raton, Fla., (1997).

Alternatively, the protein inhibitor may be produced by recombinant technology methods as known in the art and as described, for example, in Sambrook et al., *Molecular Cloning: A Laboratory Manual*, Cold Springs Harbor laboratory, $2^{nd}$ ed., Cold Springs Harbor, N.Y. (1989), Martin, Robin, *Protein Synthesis: Methods and Protocols*, Humana Press, Totowa, N.J. (1998) and *Current Protocols in Molecular Biology* (Ausubel et al., eds.), John Wiley & Sons, which is regularly and periodically updated. For example, an expression vector may be used to produce the desired peptide inhibitor in an appropriate host cell and the product may then be isolated by known methods. The expression vector may include, for example, the nucleotide sequence encoding the desired peptide wherein the nucleotide sequence is operably linked to a promoter sequence.

As defined herein, a nucleotide sequence is "operably linked" to another nucleotide sequence when it is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary to join two protein coding regions, contiguous and in reading frame. However, since enhancers may function when separated from the promoter by several kilobases and intronic sequences may be of variable length, some nucleotide sequences may be operably linked but not contiguous. Additionally, as defined herein, a nucleotide sequence is intended to refer to a natural or synthetic linear and sequential array of nucleotides and/or nucleosides, and derivatives thereof. The terms "encoding" and "coding" refer to the process by which a nucleotide sequence, through the mechanisms of transcription and translation, provides the information to a cell from which a series of amino acids can be assembled into a specific amino acid sequence to produce a polypeptide.

The inhibitor may be derived from an isozyme of PKC, such as δV1-1, whose amino acid sequence from *Rattus norvegicus* is set forth in SEQ ID NO:1 (SFNSYELGSL), representing amino acids 8-17 of rat δPKC as found in Genbank Accession No. AAH76505. Alternatively, the peptide inhibitor may be other fragments of PKC, such as δV1-2, δV1-5 and/or δV5, or some combination of δV1-1, δV1-2, δV1-5 and δV5. The amino acid sequence of δV1-2 from *Rattus norvegicus* is set forth in SEQ ID NO:2 (ALTTDRGKTLV), representing amino acids 35 to 45 of rat δPKC found in Genbank Accession No. AAH76505. The amino acid sequence of δV1-5 from *Rattus norvegicus* is set forth in SEQ ID NO:3 (KAEFWLDLQPQAKV), representing amino acids 101 to 114 of rat δPKC found in Genbank Accession No. AAH76505. The amino acid sequence of δV5 is set forth in SEQ ID NO:4, representing amino acids 569-626 of human δPKC found in Genbank Accession No. BAA01381, with the exception that amino acid 11 (aspartic acid) is substituted with a proline.

The peptide inhibitors may include natural amino acids, such as the L-amino acids or non-natural amino acids, such as D-amino acids. The amino acids in the peptide may be linked by peptide bonds or, in modified peptides described herein, by non-peptide bonds.

A wide variety of modifications to the amide bonds which link amino acids may be made and are known in the art. Such modifications are discussed in general reviews, including in Freidinger, R. M. "Design and Synthesis of Novel Bioactive Peptides and Peptidomimetics" *J. Med. Chem.* 46:5553 (2003), and Ripka, A. S., Rich, D. H. "Peptidomimetic Design" *Curr. Opin. Chem. Biol.* 2:441 (1998). These modifications are designed to improve the properties of the peptide by increasing the potency of the peptide or by increasing the half-life of the peptide.

The potency of the peptide may be increased by restricting the conformational flexibility of the peptide. This may be achieved by, for example, including the placement of additional alkyl groups on the nitrogen or alpha-carbon of the amide bond, such as the peptoid strategy of Zuckerman et al, and the alpha modifications of, for example Goodman, M. et. al. (*Pure Appl. Chem.* 68:1303 (1996)). The amide nitrogen and alpha carbon may be linked together to provide additional constraint (Scott et al, *Org. Letts.* 6:1629-1632 (2004)).

The half-life of the peptide may be increased by introducing non-degradable moieties to the peptide chain. This may be achieved by, for example, replacement of the amide bond by a urea residue (Patil et al, *J. Org. Chem.* 68:7274-7280 (2003)) or an aza-peptide link (Zega and Urleb, *Acta Chim. Slov.* 49:649-662 (2002)). Other examples of non-degradable moieties that may be introduced to the peptide chain include introduction of an additional carbon ("beta peptides", Gellman, S. H. *Acc. Chem. Res.* 31:173 (1998)) or ethene unit (Hagihara et al, *J. Am. Chem. Soc.* 114:6568 (1992)) to the chain, or the use of hydroxyethylene moieties (Patani, G. A., Lavoie, E. J. *Chem. Rev.* 96:3147-3176 (1996)) and are also well known in the art. Additionally, one or more amino acids may be replaced by an isosteric moiety such as, for example, the pyrrolinones of Hirschmann et al (*J. Am. Chem. Soc.* 122:11037 (2000)), or tetrahydropyrans (Kulesza, A. et al., *Org. Letts.* 5:1163 (2003)).

Although the peptides are described primarily with reference to amino acid sequences from *Rattus norvegicus*, it is understood that the peptides are not limited to the specific amino acid sequences set forth in SEQ ID NOS:1-4. Skilled artisans will recognize that, through the process of mutation and/or evolution, polypeptides of different lengths and having different constituents, e.g., with amino acid insertions, substitutions, deletions, and the like, may arise that are related to, or sufficiently similar to, a sequence set forth herein by virtue of amino acid sequence homology and advantageous functionality as described herein. The terms "δV1-1 peptide", "δV1-2 peptide", "δV1-5 peptide" and "δV5 peptide" are used to refer generally to the peptides having the features described herein and preferred examples include peptides having the amino acid sequence of SEQ ID NO:1, SEQ ID NO:2, SEQ ID NO:3 and SEQ ID NO:4, respectively. Also included within this definition, and in the scope of the invention, are variants of the peptides which function in increasing cerebral blood flow as described herein.

The peptide inhibitors described herein also encompass amino acid sequences similar to the amino acid sequences set forth herein that have at least about 50% identity thereto and function to increase cerebral blood flow. Preferably, the amino acid sequences of the peptide inhibitors encompassed in the invention have at least about 60% identity, further at least about 70% identity, preferably at least about 75% or 80% identity, more preferably at least about 85% or 90% identity, and further preferably at least about 95% identity, to the amino acid sequences, including SEQ ID NOS:1-4, set forth herein.

Percent identity may be determined, for example, by comparing sequence information using the advanced BLAST computer program, including version 2.2.9, available from the National Institutes of Health. The BLAST program is based on the alignment method of Karlin and Altschul. *Proc. Natl. Acad. Sci. USA* 87:2264-2268 (1990) and as discussed in Altschul, et al., *J. Mol. Biol.* 215:403-410 (1990); Karlin And Altschul, *Proc. Natl. Acad. Sci. USA* 90:5873-5877 (1993); and Altschul et al., *Nucleic Acids Res.* 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the proteins being compared. Default parameters are provided to optimize searches with short query sequences in, for example, blastp with the program. The program also allows use of an SEG filter to mask-off segments of the query sequences as determined by the SEG program of Wootton and Federhen, *Computers and Chemistry* 17:149-163 (1993).

Accordingly, fragments or derivatives of peptide inhibitors described herein may also be advantageously utilized that include amino acid sequences having the specified percent identities to SEQ ID NOS:1-4 described herein to increase cerebral blood flow. For example fragments or derivatives of δV1-1, δV1-2, δV1-5 and δV5 that are effective in inhibiting δPKC and increasing cerebral blood flow in a mammal as described herein may also advantageously be utilized in the present invention.

Conservative amino acid substitutions may be made in the amino acid sequences described herein to obtain derivatives of the peptides that may advantageously be utilized in the present invention. Conservative amino acid substitutions, as known in the art and as referred to herein, involve substituting amino acids in a protein with amino acids having similar side chains in terms of, for example, structure, size and/or chemical properties. For example, the amino acids within each of the following groups may be interchanged with other amino acids in the same group: amino acids having aliphatic side chains, including glycine, alanine, valine, leucine and isoleucine; amino acids having non-aromatic, hydroxyl-containing side chains, such as serine and threonine; amino acids having acidic side chains, such as aspartic acid and glutamic acid; amino acids having amide side chains, including glutamine and asparagine; basic amino acids, including lysine, arginine and histidine; amino acids having aromatic ring side chains, including phenylalanine, tyrosine and tryptophan; and amino acids having sulfur-containing side chains, including cysteine and methionine. Additionally, amino acids having acidic side chains, such as aspartic acid and glutamic acid, are considered interchangeable herein with amino acids having amide side chains, such as asparagine and glutamine.

Accordingly, modifications to δV1-1 that are expected to result in effective inhibition of δPKC and a concomitant increase in cerebral blood flow include the following changes to SEQ ID NO:1 shown in lower case: tFNSYELGSL (SEQ ID NO:5), aFNSYELGSL (SEQ ID NO:6), SFNSYELGtL (SEQ ID NO:7), including any combination of these three substitutions, such as tFNSYELGtL (SEQ ID NO:8). Other potential modifications include SyNSYELGSL (SEQ ID NO:9), SFNSfELGSL (SEQ ID NO:10), SNSYdLGSL (SEQ ID NO:11), SFNSYELpSL (SEQ ID NO:12).

Other possible modifications that are expected to produce a peptide that functions in the invention include changes of one or two L to I or V, such as SFNSYEiGSv (SEQ ID NO:13), SFNSYEvGSi (SEQ ID NO:14), SFNSYELGSv (SEQ ID NO:15), SFNSYELGSi (SEQ ID NO:16), SFNSYEiGSL (SEQ ID NO:17), SFNSYEvGSL (SEQ ID NO:18), aFNSYELGSL (SEQ ID NO:19), any combination of the above-described modifications, and other conservative amino acid substitutions described herein.

Fragments and modification of fragments of δV1-1 are also contemplated, including: YELGSL (SEQ ID NO:20), YdLGSL (SEQ ID NO:21), fdLGSL (SEQ ID NO:22), YdiGSL (SEQ ID NO:23), iGSL (SEQ ID NO:24), YdvGSL (SEQ ID NO:25), YdLpsL (SEQ ID NO:26), YdLgiL (SEQ ID NO:27), YdLGSi (SEQ ID NO:28), YdLGSv (SEQ ID NO:29), LGSL (SEQ ID NO:30), iGSL (SEQ ID NO:31), vGSL (SEQ ID NO:32), LpSL (SEQ ID NO:33), LGiL (SEQ ID NO:34), LGSi (SEQ ID NO:35), LGSv (SEQ ID NO:36).

Accordingly, the term "a δV1-1 peptide" as used herein further refers to a peptide identified by SEQ ID NO:1 and to a peptide having an amino acid sequence having the specified percent identity described herein to the amino acid sequence of SEQ ID NO:1, including but not limited to the peptides set forth in SEQ ID NOS:5-19, as well as fragments of any of these peptides that retain activity for increasing cerebral blood flow as described herein, as exemplified by but not limited to SEQ ID NOS:20-36.

Modifications to δV1-2 that are expected to result in effective inhibition of δPKC and a concomitant increase in cerebral blood flow include the following changes to SEQ ID NO:2 shown in lower case: ALsTDRGKTLV (SEQ ID NO:37), ALTsDRGKTLV (SEQ ID NO:38), ALTTDRGKsLV (SEQ ID NO:39), and any combination of these three substitutions, ALTTDRpKTLV (SEQ ID NO:40), ALTTDRGrTLV (SEQ ID NO:41), ALTTDkGKTLV (SEQ ID NO:42), ALTTDkGkTLV (SEQ ID NO:43), changes of one or two L to I, or V and changes of V to I, or L and any combination of the above. In particular, L and V can be substituted with V, L, I R and D, E can be substituted with N or Q. One skilled in the art would be aware of other conservative substitutions that may be made to achieve other derivatives of δV1-2 in light of the description herein.

Accordingly, the term "a δV1-2 peptide" as further used herein refers to a peptide identified by SEQ ID NO:2 and to a peptide having an amino acid sequence having the specified percent identity described herein to the amino acid sequence of SEQ ID NO:2, including but not limited to the peptides set forth in SEQ ID NOS:37-43, as well as fragments of any of these peptides that retain activity for increasing cerebral blood flow as described herein.

Modifications to δV1-5 that are expected to result in effective inhibition of δPKC and a concomitant increase in cerebral blood flow as described herein include the following changes to SEQ ID NO:3 shown in lower case:

```
rAEFWLDLQPQAKV;      (SEQ ID NO: 44)

KAdFWLDLQPQAKV;      (SEQ ID NO: 45)

KAEFWLeLQPQAKV,      (SEQ ID NO: 46)

KAEFWLDLQPQArV,      (SEQ ID NO: 47)

KAEyWLDLQPQAKV,      (SEQ ID NO: 48)

KAEFWiDLQPQAKV,      (SEQ ID NO: 49)
```

-continued

| | |
|---|---|
| KAEFWvDLQPQAKV, | (SEQ ID NO: 50) |
| KAEFWLDiQPQAKV, | (SEQ ID NO: 51) |
| KAEFWLDvQPQAKV, | (SEQ ID NO: 52) |
| KAEFWLDLnPQAKV, | (SEQ ID NO: 53) |
| KAEFWLDLQPnAKV, | (SEQ ID NO: 54) |
| KAEFWLDLQPQAKi, | (SEQ ID NO: 55) |
| KAEFWLDLQPQAKI, | (SEQ ID NO: 56) |
| KAEFWaDLQPQAKV, | (SEQ ID NO: 57) |
| KAEFWLDaQPQAKV, and | (SEQ ID NO: 58) |
| KAEFWLDLQPQAKa. | (SEQ ID NO: 59) |

Fragments of δV1-5 are also contemplated, including:

| | |
|---|---|
| KAEFWLD, | (SEQ ID NO: 60) |
| DLQPQAKV, | (SEQ ID NO: 61) |
| EFWLDLQP, | (SEQ ID NO: 62) |
| LDLQPQA, | (SEQ ID NO: 63) |
| LQPQAKV, | (SEQ ID NO: 64) |
| AEFWLDL, and | (SEQ ID NO: 65) |
| WLDLQPQ. | (SEQ ID NO: 66) |

Modifications to fragments of δV1-5 are also contemplated and include the modifications shown for the full-length fragments as well as other conservative amino acid substitutions described herein. The term "a δV1-5 peptide" as further used herein refers to SEQ ID NO:3 and to a peptide having an amino acid sequence having the specified percent identity described herein to an amino acid sequence of SEQ ID NO:3, as well as fragments thereof that retain activity for increasing cerebral blood flow as described herein.

Modifications to δV5 that are expected to result in effective inhibition of δPKC and a concomitant increase in cerebral blood flow as described herein include making one or more conservative amino acid substitutions, including substituting: R at position 3 with Q: S at position 8 with T; F at position 15 with W; V at position 6 with L and D at position 30 with E; K at position 31 with R; and E at position 53 with D, and various combinations of these modifications and other modifications that can be made by the skilled artisan in light of the description herein.

Fragments of δV5 are also contemplated, and include, for example, the following:

| | |
|---|---|
| SPRPYSNF, | (SEQ ID NO: 67) |
| RPYSNFDQ, | (SEQ ID NO: 68) |
| SNFDQEFL, | (SEQ ID NO: 69) |
| DQEFLNEK, | (SEQ ID NO: 70) |
| FLNEKARL, | (SEQ ID NO: 71) |
| LIDSMDQS, | (SEQ ID NO: 72) |
| SMDQSAFA, | (SEQ ID NO: 73) |
| DQSAFAGF; | (SEQ ID NO: 74) |
| FVNPKFEH, | (SEQ ID NO: 75) |
| KFEHLLED, | (SEQ ID NO: 76) |
| NEKARLSY, | (SEQ ID NO: 77) |
| RLSYSDKN, | (SEQ ID NO: 78) |
| SYSDKNLI, | (SEQ ID NO: 79) |
| DKNLIDSM, | (SEQ ID NO: 80) |
| PFRPKVKS, | (SEQ ID NO: 81) |
| RPKVKSPR, and | (SEQ ID NO: 82) |
| VKSPRPYS. | (SEQ ID NO: 83) |

Modifications to fragments of δV5 are also contemplated and include the modifications shown for the full-length fragments as well as other conservative amino acid substitutions described herein. The term "a δV5 peptide" as further used herein refers to SEQ ID NO:4 and to a peptide having an amino acid sequence having the specified percent identity described herein to an amino acid sequence of SEQ ID NO:4, as well as fragments thereof that retain activity for increasing cerebral blood flow. The inhibitors used for treatment herein may include a combination of the peptides described herein.

Other suitable molecules or compounds, including small molecules, that may act as inhibitors of δPKC may be determined by methods known to the art. For example, such molecules may be identified by their ability to inhibit translocation of δPKC to its subcellular location. Such assays may utilize, for example, fluorescently-labeled enzyme and fluorescent microscopy to determine whether a particular compound or agent may aid in the cellular translocation of δPKC. Such assays are described, for example, in Schechtman, D. et al., *J. Biol. Chem.* 279(16):15831-15840 (2004) and include use of selected antibodies. Other assays to measure cellular translocation include Western blot analysis as described in Dorn, G. W., II et al., *Proc. Natl. Acad. Sci. U.S.A.* 96(22): 12798-12803 (1999) and Johnson, J. A. and Mochly-Rosen, D., *Circ Res.* 76(4):654-63 (1995).

The inhibitors may be modified by being part of a fusion protein. The fusion protein may include a protein or peptide that functions to increase the cellular uptake of the peptide inhibitors, has another desired biological effect, such as a therapeutic effect, or may have both of these functions. For example, it may be desirable to conjugate or otherwise attach, the δV1-1 peptide, or other peptides described herein, to a cytokine or other protein that elicits a desired biological response. The fusion protein may be produced by methods known to the skilled artisan. The inhibitor peptide may be bound, or otherwise conjugated, to another peptide in a variety of ways known to the art. For example, the inhibitor peptide may be bound to a carrier peptide, such as a cell permeable carrier peptide, or other peptide described herein via cross-linking wherein both peptides of the fusion protein retain their activity. As a further example, the peptides may be linked or otherwise conjugated to each other by an amide bond from the C-terminal of one peptide to the N-terminal of the other peptide. The linkage between the inhibitor peptide and the other member of the fusion protein may be non-cleavable with a peptide bond, or cleavable with, for example, an ester or other cleavable bond known to the art.

Furthermore, in other forms of the invention, the carrier protein, such as a cell permeable carrier peptide, or other peptide that may increase cellular uptake of the peptide inhibitor may be, for example, a *Drosophila* Antennapedia homeodomain-derived sequence which is set forth in SEQ ID NO:84 (CRQIKIWFQNRRMKWKK), and may be attached to the inhibitor by cross-linking via an N-terminal Cys-Cys bond as discussed in Theodore, L., et al. *J. Neurosci.* 15:7158-7167 (1995); Johnson, J. A., et al. *Circ. Res* 79:1086 (1996). Alternatively, the inhibitor may be modified by a Transactivating Regulatory Protein (Tat)-derived transport polypeptide (such as from amino acids 47-57 of Tat shown in SEQ ID NO:85; YGRKKRRQRRR) from the Human Immunodeficiency Virus, Type 1, as described in Vives, et al., *J. Biol. Chem,* 272:16010-16017 (1997), U.S. Pat. No. 5,804,604 and Genbank Accession No. AAT48070; or with polyarginine as described in Mitchell, et al. *J. Peptide Res.* 56:318-325 (2000) and Rothbard, et al., *Nature Med.* 6:1253-1257 (2000). The inhibitors may be modified by other methods known to the skilled artisan in order to increase the cellular uptake of the inhibitors.

The inhibitors may be advantageously administered in various forms. For example, the inhibitors may be administered in tablet form for sublingual administration, in a solution or emulsion. The inhibitors may also be mixed with a pharmaceutically-acceptable carrier or vehicle. The vehicle may be a liquid, suitable, for example, for parenteral administration, including water, saline or other aqueous solution, or may be an oil or an aerosol. The vehicle may be selected for intravenous or intraarterial administration, and may include a sterile aqueous or non-aqueous solution that may include preservatives, bacteriostats, buffers and antioxidants known to the art. In the aerosol form, the inhibitor may be used as a powder, with properties including particle size, morphology and surface energy known to the art for optimal dispersability. In tablet form, a solid vehicle may include, for example, lactose, starch, carboxymethyl cellulose, dextrin, calcium phosphate, calcium carbonate, synthetic or natural calcium allocate, magnesium oxide, dry aluminum hydroxide, magnesium stearate, sodium bicarbonate, dry yeast or a combination thereof. The tablet preferably includes one or more agents which aid in oral dissolution. The inhibitors may also be administered in forms in which other similar drugs known in the art are administered.

The inhibitors utilized are capable of chronic administration without causing desensitization of the patient to the inhibitor. That is, the inhibitors can be administered multiple times, or after a prolonged period of time including one, two or three or more days; one two, or three or more weeks or several months to a patient and will continue to cause an increase in the flow of blood in the respective blood vessel.

The inhibitors may be administered to a patient by a variety of routes. For example, the inhibitors may be administered parenterally, including intraperitoneally; intravenously; intraarterially; subcutaneously, or intramuscularly. The inhibitors may also be administered via a mucosal surface, including rectally, and intravaginally; intranasally; by inhalation, either orally or intranasally; orally, including sublingually; intraocularly and transdermally. Combinations of these routes of administration are also envisioned. A preferred mode of administration is by infusion or reperfusion through the occluded or partially-occluded cerebral artery, or an artery that is connected to such an occluded or partially-occluded artery. By "partially-occluded cerebral artery" it is meant herein a cerebral artery in which blood flow is reduced after a blood flow reducing event affecting the brain blood vessels when compared to blood flow prior to such event or attack. Such blood flow reducing events include an ischemic attack or other hypoxic event, and vasoconstriction or vasospasm which may follow, for example, a hemorrhagic stroke. Included in the definition of "partially-occluded cerebral artery" is a cerebral artery in which blood flow is reduced compared to a baseline or standard blood flow rate for that blood vessel. Such rates are known to the skilled artisan.

A therapeutically effective amount of the inhibitor is provided. As used herein, a therapeutically effective amount of the inhibitor is the quantity of the inhibitor required to increase blood flow in a mammalian brain blood vessel and/or to reduce the cell, tissue or organ damage or death that occurs due to various cell damaging events, including an ischemic attack, vasoconstriction or a vasospasm, including following a hemorrhagic stroke; due to chronic high blood pressure; and/or due to idiopathic causes. This amount will vary depending on the time of administration (e.g., prior to an ischemic event, at the onset of the event or thereafter), the route of administration, the duration of treatment, the specific inhibitor used and the health of the patient as known in the art. The skilled artisan will be able to determine the optimum dosage. Generally, the amount of inhibitor typically utilized may be, for example, about 0.0005 mg/kg body weight to about 50 mg/kg body weight, but is preferably about 0.05 mg/kg to about 0.5 mg/kg.

The amount of inhibitor is preferably sufficient to increase the flow of blood by at least about 5%, preferably at least about 25%, further at least about 50%, more preferably at least about 75% and further at least about 100% compared to the flow of blood prior to the treatment, including, for example, during the onset of an ischemic event or after a specified time period after the onset of an aforementioned event, such as up to about 24 hours after the onset. The blood flow is increased by the above-recited levels typically when compared to the flow of blood at the onset of an aforementioned event, or about 2 hours, about 3 hours or about 6 hours after the onset of the event. It is understood that increases in blood flow larger than those recited above may also be obtained.

The blood vessels in which the blood flow may be increased include any of the blood vessels of the brain in which increased blood flow is desired. Such vessels also include those which may be totally or partially occluded, which may be susceptible to occlusion, as well as those vessels which have been exposed to a hypoxic event, such as an ischemic stroke, or other event, such as vasoconstriction or vasospasm, which decreases delivery of cellular nutrients, including glucose. Such vessels include, for example, cerebral arteries, such as the anterior cerebral artery, the middle cerebral artery and the posterior cerebral artery. Brain, or other, blood vessels that supply blood to the other brain blood vessels may also be treated to increase the blood flow as described herein. Such blood vessels include, for example, the vertebral arteries and the carotid arteries, such as the internal carotid arteries, the common carotid arteries and the external carotid arteries. Blood flow in arteries that branch from the aforementioned arteries may also be increased as described in the present invention. For example, the lenticulostriate arteries which branch from the middle cerebral artery, may be treated according to the methods described herein. Blood flow may further be increased in the cerebral microvascular capillaries and arterioles, and such vessels are well known in the art. This list of brain blood vessels amenable for treatment to increase cerebral blood flow therein is not exhaustive. In light of the description herein, one skilled in the art is aware of other brain blood vessels that may be treated according to the methods described herein.

The patient to be treated is typically one in need of such treatment, including one that is susceptible to, or has experienced, a decrease in cerebral blood flow from one of a number of events, such as an ischemic or hypoxic event or otherwise has the potential to incur cellular, tissue or organ damage as a result of such events. The patients can include those experiencing, or who are otherwise prone to experiencing, decreased cerebral blood flow due to vasoconstriction or vasospasm following hemorrhagic stroke; chronic high blood pressure and/or or due to idiopathic causes. The patient is furthermore typically a vertebrate, preferably a mammal, and including a human. Other animals which may be treated include farm animals, such as horse, sheep, cattle, and pigs. Other exemplary animals that may be treated include cats, dogs; rodents, including those from the order Rodentia, such as mice, rats, gerbils, hamsters, and guinea pigs; members of the order Lagomorpha, including rabbits and hares, and any other mammal that may benefit from such treatment. The patient is preferably treated in vivo, preferably at the onset of an ischemic event. The patient may also be treated after about 1 minute to about 10 hours, but preferably between about 1 minute to about 2 hours, and further preferably after no more than about 24 hours, after occurrence of the ischemic or other event leading to hypoxia and/or cellular nutrient deprivation.

The patient is typically one who can benefit from increased cerebral blood flow. For example, a patient who has experienced a hypoxic event, such as an ischemic stroke, or who has vasoconstriction or vasospasm following hemorrhagic stroke; due to chronic high blood pressure; and/or due to idiopathic causes may benefit from increased blood flow to the ischemic penumbra as previously mentioned herein.

The ischemic penumbra, which is potentially salvageable tissue, may be identified in a patient by methods known to the skilled artisan. For example, the ischemic penumbra may be identified by observing differences in the abnormal region defined by perfusion-weighted imaging and diffusion-weighted imaging as described in Duong, T. Q. and Fisher, M., *Curr. Atheroscl. Rep.* 6:267-273 (2004). This difference in the defined regions is known as the perfusion-diffusion mismatch. The perfusion-diffusion mismatch region is presumed to approximate the ischemic penumbra. Vasoconstriction and vasospasm are usually detected using digital subtraction angiography as known in the art.

In yet another aspect of the invention, kits for increasing blood flow in a vertebrate, including a mammalian, brain blood vessel characterized by, or otherwise experiencing, decreased blood flow due to a disease or condition, including an ischemic event, vasoconstriction or vasospasm following, for example, a hemorrhagic stroke; due to chronic high blood pressure; and/or due to idiopathic causes are provided. In one form, a kit includes an inhibitor of δPKC and instructions for using the inhibitor as described herein to increase blood flow in the respective brain blood vessel. In certain forms of the invention, the inhibitor is a δV1-1, δV1-2, δV1-5 or a δV5 peptide as described herein, or fragments or derivatives of these peptides as described herein, or some combination of these peptides, their fragments and/or their derivatives. The kit may further include a syringe or other similar device known in the art for administering the inhibitor. The components of the kit are placed in a container, such as a box, and each component is spaced relative to each other in the box. The inhibitors may be contained in a sterilized vial or similar container. If the inhibitors are provided in dried or lyophilized form and require reconstitution, the kit may further include a pharmaceutically-acceptable carrier as previously described herein in a sterilized vial or similar container. A preferred carrier is a sterile solution as described herein to dissolve the inhibitor.

Reference will now be made to specific examples illustrating the invention described above. It is to be understood that the examples are provided to illustrate preferred embodiments and that no limitation to the scope of the claims is intended thereby.

EXAMPLE 1

Increased Cerebral Blood Flow in Rats Subjected to Ischemic/Reperfusion Injury The present example shows that increased blood flow was achieved in a rat middle cerebral artery by treating the rat with a δV1-1 peptide.

Materials

Male Sprague-Dawley rats (280-320g; n=8) were used for cerebral ischemia and reperfusion, and subsequent monitoring of cerebral blood flow. Tat or δV1-1 peptides were synthesized and conjugated via a Cys S—S bond as described previously (Chen, et al., *Proc. Natl. Acad. Sci. USA* 25(20): 11114-11119 (2001); Inagaki, et al., *Circulation* 11(108): 2304-2307 (2003)). Rats were sacrificed by overdose of isoflurane immediately following procedure Methods Ischemia and reperfusion were induced in male Sprague-Dawley rats using an occluding intraluminal suture as described in Maier, et al., *J. Neurosurg.* 94(1):90-96 (2001). Briefly, an uncoated 30 mm long segment of 3-0 nylon monofilament suture with the tip rounded by a flame was inserted into the stump of the external carotid artery and advanced into the internal carotid artery 19-20 mm from the bifurcation to occlude the ostium of the middle cerebral artery (MCA). Following placement of the suture, the wound was closed and animals were placed back in cages for a period of two hours. Following this period, animals were reanestheized and the suture was withdrawn to allow reperfusion of the brain.

Immediately following reperfusion, the rats were placed in a stereotaxic frame, and a burr hole was drilled through the skull 1 mm posterior and 6 mm lateral to the bregma on the ipsilateral hemisphere corresponding to the ischemic territory. Cerebral blood flow (CBF) was measured via this burr hole using a laser Doppler probe controlled by a micromanipulator (Laserflo BPM403A laser-Doppler flowmeter, Vasamedic, St. Paul, Minn.). The display is digital only, collects eight data points per second, and was set to give a moving average of data every 0.1 sec. (Perez-Pinzon, et al., *J. Neurolog. Sci.* 153 (1):25-31 (1997); Borlongan, et al., *Brain Res.* 1010(1-2):108-116 (2004)). CBF readings began at 30 minutes from the onset of reperfusion. Following a period of 20-30 minutes to establish baseline CBF, a δPKC inhibitor, the δV1-1 peptide (which was conjugated to Tat for delivery), was injected by intraperitoneal bolus, and blood flow was monitored for an additional 20-30 minutes. Sham animals did not receive ischemia, but were otherwise similarly treated.

Results

Figure 2:
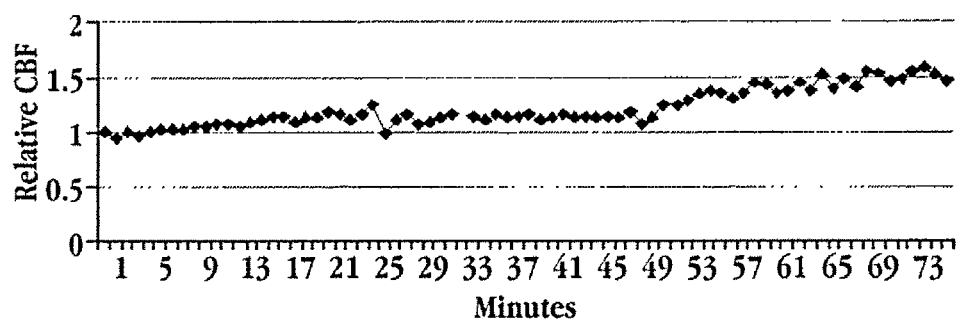
FIG. 2 depicts a graph of CBF as a function of time in rats subjected to ischemic/reperfusion injury by middle cerebral artery (MCA) occlusion and treated with a therapeutic dosage of δV1-1 as more fully described in Example 1. The arrow denotes delivery of δV1-1 peptide.

It was found that bolus, intraperitoneal delivery of the δV1-1 peptide increased cerebral blood flow within 30 minutes, in rats subjected to ischemic/reperfusion injury as shown in FIG. 2. Sham-treated animals showed no change in blood flow following treatment with the δV1-1 peptide within 30 minutes of delivery as seen in FIG. 1. In addition, delivery of saline alone or Tat control peptides had no effect on CBF in either sham or ischemia treated animals (data not shown).

EXAMPLE 2

Effect of Chronic Administration of an Inhibitor of δPKC on Cerebral Blood Flow in Rats Subjected to Ischemic/Reperfusion Injury The present example shows that rats subjected to ischemic/reperfusion injury and treated multiple times with a δV1-1 peptide did not become desensitized to the inhibitor. The experiment was carried out as described in Example 1.

Results

Figure 3:
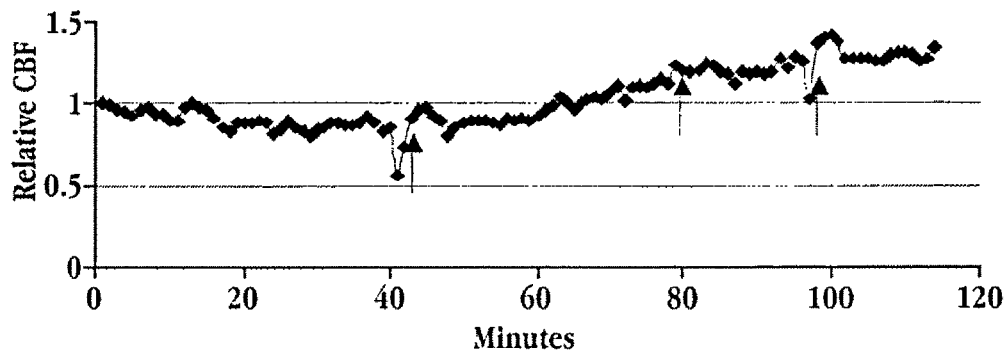
FIG. 3 shows a graph of CBF as a function of time in rats subjected to ischemic/reperfusion injury and treated with repeated administrations of a therapeutic dosage of δV1-1 as more fully described in Example 2. The arrows denote delivery of δV1 -1 peptide.

Repeated intraperitoneal administrations of δV1-1 peptide further increased blood flow as shown in FIG. 3.

EXAMPLE 3

Microscopy Inspection of Brain Tissue in Rats Subjected to Ischemic/Reperfusion Injury The present example shows that delivery of δV1-1-TAT following stroke improves cerebrovascular pathology. More specifically, intraperitoneal delivery of δV1-1-TAT following middle cerebral artery occlusion increased the number of patent microvessels and improved microvascular pathology in the ischemic penumbra following stroke.

Methods

Sprague-Dawley rats underwent 120 minutes MCA occlusion, followed by 4 hrs of reperfusion. Rats were treated with either TAT or δV1-1-TAT peptides at the onset of reperfusion by bolus intraperitoneal injection (0.2 mg/kg in 1 mL, n=4 per group). Sham animals were similarly treated, but did not undergo ischemia, and did not receive peptides (n=4). Following the reperfusion period, rats were heavily anesthetized using isoflurane, and underwent transcardial perfusion using 0.7% NaCl/PBS followed by 4% formaldehyde in 0.7% NaCl/PBS.

Brains were removed and kept at 4° C. overnight in 2% formaldehyde/2% glutaraldehyde in 0.1M sodium cacodylate buffer, pH 7.3, Brain sections (~1 mm$^3$) were then dissected from the cortical surface, at ~1 mm anterior/~6 mm lateral to bregma on the ipsilateral cortex (corresponding to the area measured by laser Doppler flowmetry). Tissue was post-fixed in 1% osmium tetroxide for 1 hr, washed with water, and stained in 1% uranyl acetate solution. Tissue was dehydrated using an ethanol gradient followed by 100% propylene oxide, and infiltrated with Epon and Embed 812 medium, placed in molds, and polymerized overnight at 65° C. before slicing. Sections (75 and 90 nm) were picked up on formvar/Carbon coated Cu grids, stained for 15 seconds in 1:1 Super-saturated uranyl acetate (7.7%) in acetone followed by staining in 0.2% lead citrate for 3 to 4 minutes (all reagents from Electron Microscopy Sciences, PA). Tissue was observed in the JEOL 1230 transmission electron microscope (TEM) at 80 kV and photos were taken using a Gatan Multiscan 791 digital camera.

To quantitate number of patent vessels, 10-15 non-overlapping fields (1200× magnification) were photographed from 2-3 slices taken from each animal. Vessels were identified and counted if lumen and endothelial lining was apparent; vessels were confirmed by scanning over these fields at higher magnification. Assessments of vessel count were performed by an observer blinded to treatment group. The number of vessels per field was then averaged for each group of animals (n=4 per group). Statistical differences between groups were analyzed using an unpaired t-test. Higher magnification images (5000-15000×) were taken to assess microvascular morphology.

Results

Figure 4A:
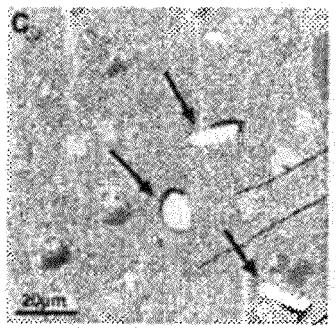
Figure 4B:
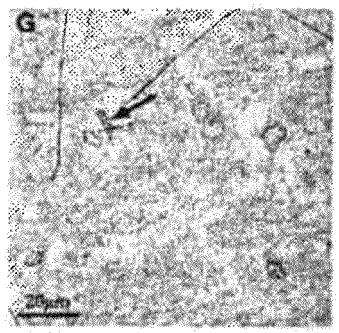
Figure 4C:
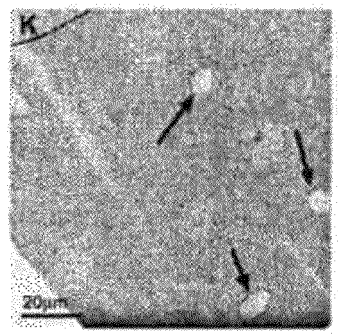
Figure 4D:
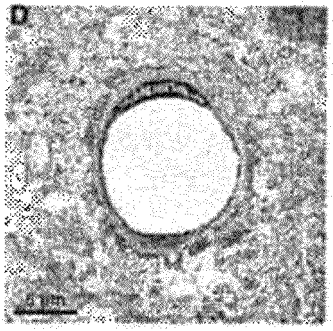
Figure 4E:
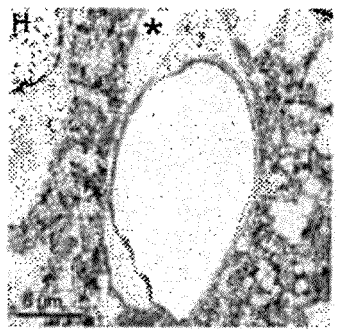
Figure 4F:
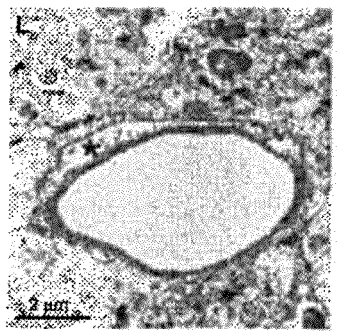
Figure 5:
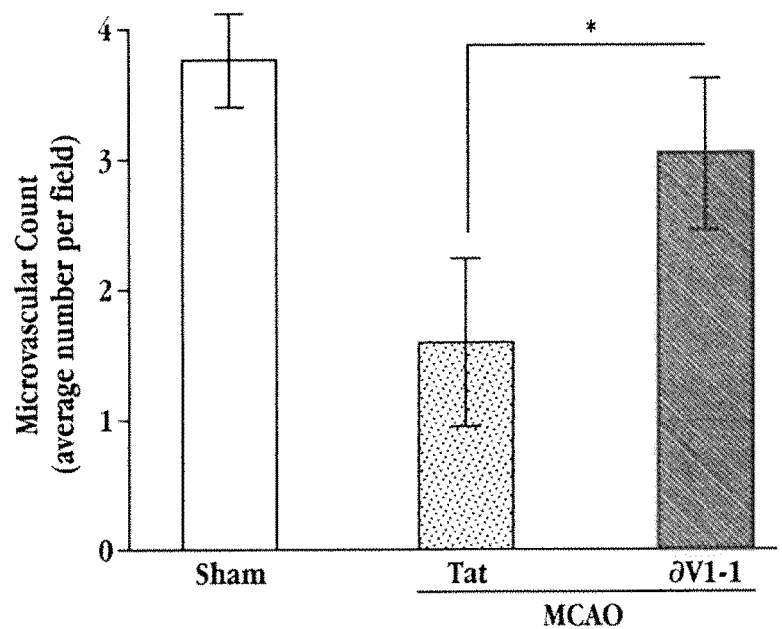
FIG. 5 is a bar graph of the average number of microvascular vessels in the microscope field for animals subjected to ischemic/reperfusion injury by middle cerebral artery (MCA) occlusion and treated with TAT peptide or with δV1-1-TAT-treated tissue Sham treated animals were similarly treated, but were not subjected to ischemic/reperfusion injury or delivery of peptides.

Defined regions of the cerebral cortex corresponding to the ischemic penumbra (1 mm posterior/6 mm lateral to bregma) were examined. Lower magnification images (1200×) were first used to quantitate microvessel number, and these images are shown in FIGS. 4A-4C. Vessels were counted if a recognizable microvascular lumen and surrounding endothelial lining was identified. In ischemic animals treated with TAT peptide, a significant reduction in the number of vessels was observed compared with δV1-1-TAT treated tissue (TAT, 1.6±0.6 vessels/field; δV1-1-TAT, 3.1±0.6 vessels/field; $p<0.05$; n=4; FIG. 5 and FIGS. 4D-4F). The number of microvessels in animals subject to ischemia followed with δV1-1TAT treatment at reperfusion was similar to that in sham animals (sham, 3.8+/−0.4 vessels/field; n.s.; n=4; FIG. 5 and FIG. 4C vs. FIG. 4A).

Features of healthy microvascular structure were observed using higher magnification TEM in cortical tissue from sham control animals. These included intact basal lamina, clear and patent vessel lumens and lack of abnormal perivascular spaces (FIGS. 4D, 4G, 4J). Evidence of ultrastructural damage in brain tissue from ischemic animals was observed (FIG. 4I, 4J), including signs of vascular edema, swollen astrocyte end-foot processes, enlarged endothelial nuclei, breakdown of the basal lamina, compression of vascular lumen, and luminal surface irregularities. However, in ischemic animals treated with δV1-1-TAT (0.2 mg/kg) at reperfusion only, microvascular structure appeared significantly less damaged (FIGS. 4F, 4I, 4L); some astrocyte end-foot swelling was observed in a small number of vessels (FIG. 4F), however most vessels appeared normal (FIGS. 4I, 4L).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A kit comprising a peptide inhibitor of δPKC consisting of a sequence of eight contigiuous amino acid residues of SEQ ID NO:4, and instructions for use.

2. The kit of claim 1, wherein said sequence is selected from the group consisting of SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, and SEQ ID NO:83.

3. The kit of claim 1, further comprising a pharmaceutically acceptable carrier or vehicle.

4. The kit of claim 3, wherein said inhibitor is mixed with said pharmaceutically acceptable carrier or vehicle.

5. A kit comprising a peptide inhibitor of δPKC consisting of a sequence of eight contiguous amino acid residues of SEQ ID NO:4, a cell-permeable carrier peptide, and instructions for use, wherein the peptide inhibitor is attached to the carrier peptide.

6. The kit of claim 5, wherein said sequence is selected from the group consisting of SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, and SEQ ID NO:83.

7. The kit of claim 5, wherein said carrier peptide is selected from the group consisting of a *Drosophila* Antennapedia homeodomain peptide, a Transactivating Regulatory Protein (Tat) peptide, and a polyarginine peptide.

8. The kit of claim 5, wherein said carrier peptide amino acid sequence is SEQ ID NO:84.

9. The kit of claim 5, wherein said carrier peptide amino acid sequence is SEQ ID NO:85.

10. The kit of claim 5, further comprising a pharmaceutically acceptable carrier or vehicle.

11. The kit of claim 10, wherein said inhibitor is mixed with said pharmaceutically acceptable carrier or vehicle.

12. A kit comprising a peptide inhibitor of δPKC consisting of a sequence of eight contiguous amino acid residues of SEQ ID NO:4 and an N-terminal Cys, a cell-permeable carrier peptide, and instructions for use, wherein the peptide inhibitor is attached to the carrier peptide.

13. The kit of claim 12, wherein said sequence is selected from the group consisting of SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, and SEQ ID NO:83.

14. The kit of claim 12, wherein said carrier peptide comprises an N-terminal Cys, and wherein said inhibitor is crosslinked to said carrier peptide via a Cys-Cys bond.

15. The kit of claim 12, wherein said carrier peptide is selected from the group consisting of a *Drosophila* Antennapedia homeodomain peptide, a Transactivating Regulatory Protein (Tat) peptide, and a polyarginine peptide.

16. The kit of claim 15, wherein said carrier peptide amino acid sequence is SEQ ID NO:84.

17. The kit of claim 12, wherein said carrier peptide amino acid sequence is SEQ ID NO:85.

18. The kit of claim 12, further comprising a pharmaceutically acceptable carrier or vehicle.

19. The kit of claim 18, wherein said inhibitor is mixed with said pharmaceutically acceptable carrier or vehicle.

* * * * *